(12) United States Patent
Rodriguez Sarmiento et al.

(10) Patent No.: US 7,087,612 B2
(45) Date of Patent: Aug. 8, 2006

(54) 3H-QUINAZOLIN-4-ONE DERIVATIVES AS MAO-B INHIBITORS

(75) Inventors: Rosa Maria Rodriguez Sarmiento, Basel (CH); Andrew William Thomas, Birsfelden (CH); Rene Wyler, Zurich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 222 days.

(21) Appl. No.: 10/734,949

(22) Filed: Dec. 13, 2003

(65) Prior Publication Data

US 2004/0142951 A1    Jul. 22, 2004

(30) Foreign Application Priority Data

Dec. 13, 2002  (EP) .................. 02027700

(51) Int. Cl.
*A61K 31/517* (2006.01)
*A01N 43/54* (2006.01)
*C07D 239/72* (2006.01)
*A61P 25/28* (2006.01)
*C07C 43/20* (2006.01)
*C07C 63/04* (2006.01)

(52) U.S. Cl. ................... 514/266.3; 544/286
(58) Field of Classification Search ......... 514/266.3; 544/286
See application file for complete search history.

(56) References Cited

U.S. PATENT DOCUMENTS 4,668,682 A * 5/1987 Sekiya et al. ............ 514/266.2
5,783,577 A * 7/1998 Houghten et al. .......... 514/247
6,890,930 B1 * 5/2005 Medreski et al. ........ 514/266.2

FOREIGN PATENT DOCUMENTS

| WO | WO 96/40095 | 12/1996 |
|----|----|----|
| WO | WO 97/33572 | 9/1997 |
| WO | WO 99 10349 | 3/1999 |
| WO | WO 01/34172 | 5/2001 |

OTHER PUBLICATIONS

Bach et al., Proc. Natl. Acad. Sci. vol. 85: pp. 4934-4938 (1988).
Cesura & Pletscher, Prog. Drug Research vol. 38: pp. 171-297 (1992).
Fowler et al., J. Neural. Transm. vol. 49: pp. 1-20 (1980).
Benedetti et al., Biochem. Pharmacol. vol. 38: pp. 555-561 (1989).
Saura et al., Neuroscience vol. 70: pp. 755-774 (1996).
Bentué-Ferrer et al., CNS Drugs vol. 6: pp. 217-236 (1996).
Gardner et al. J. Clin. Psychiatry vol. 57: pp. 99-104 (1996).
Schlaeger & Christensen, Cytotechnology vol. 30: pp. 71-83 (1999).
Zhou & Panchuk-Voloshina, Analytical Biochemistry vol. 253: pp. 169-174 (1997).

* cited by examiner

*Primary Examiner*—James O. Wilson
*Assistant Examiner*—Tamthom N. Truong
(74) *Attorney, Agent, or Firm*—George W. Johnston; Patricia S. Rocha-Tramaloni; Kimberly J. Prior

(57) ABSTRACT

This invention relates to 3H-quinazolin-4-one derivatives as defined in the specification and claims, to a process for their preparation, to pharmaceutical compositions comprising them and to their use as selective monoamine oxidase B inhibitors.

50 Claims, No Drawings

3H-QUINAZOLIN-4-ONE DERIVATIVES AS MAO-B INHIBITORS

FIELD OF THE INVENTION

The present invention relates to 3H-quinazolin-4-one derivatives, to processes for their preparation, and to pharmaceutical compositions containing them. These compounds are selective monoamine oxidase inhibitors and, therefore, are useful for treating or preventing diseases mediated by monoamine oxidase B, such as Alzheimer's disease and senile dementia.

BACKGROUND OF THE INVENTION

Monoamine oxidase (MAO, EC 1.4.3.4) is a flavin-containing enzyme responsible for the oxidative deamination of endogenous monoamine neurotransmitters such as dopamine, serotonin, adrenaline, or noradrenaline, and trace amines, e.g. phenylethylamine, as well as a number of amine xenobiotics. The enzyme exists in two forms, MAO-A and MAO-B, encoded by different genes [Bach et al., Proc. Natl. Acad. Sci. USA 85:4934–4938 (1988)] and differing in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidised by both isoforms. MAO-B is widely distributed in several organs including brain [Cesura and Pletscher, Prog. Drug Research 38:171–297 (1992)]. Brain MAO-B activity appears to increase with age. This increase has been attributed to the gliosis associated with aging [Fowler et al., J. Neural. Transm. 49:1–20 (1980)]. Additionally, MAO-B activity is significantly higher in the brains of patients with Alzheimer's disease [Dostert et al., Biochem. Pharmacol. 38:555–561 (1989)] and it has been found to be highly expressed in astrocytes around senile plaques [Saura et al., Neuroscience 70:755–774 (1994)]. In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B. Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is, e.g., discussed by Bentué-Ferrer et al. in CNS Drugs 6:217–236 (1996). Whereas a major limitation of irreversible and non-selective MAO inhibitor activity is the need to observe dietary precautions due to the risk of inducing a hypertensive crisis when dietary tyramine is ingested, as well as the potential for interactions with other medications [Gardner et al., J. Clin. Psychiatry 57:99–104 (1996)], these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

SUMMARY OF THE INVENTION

The present invention relates to 3H-quinazolin-4-one derivatives, to processes for their preparation, and to pharmaceutical compositions containing them. These compounds are selective monoamine oxidase inhibitors and, therefore, are useful for treating or preventing diseases mediated by monoamine oxidase B, such as Alzheimer's disease and senile dementia.

In a first aspect the present invention provides a compound of formula I

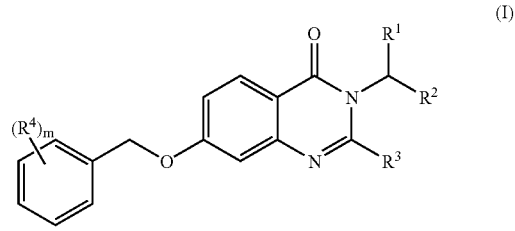

wherein
$R^1$ is —$(CH_2)_n$—CO—$NR^5R^6$; —$(CH_2)_n$—$COOR^7$; —$(CH_2)_n$—$NR^5R^6$; —$(CH_2)_n$—CN; —$(CH_2)_n$—$OR^8$; or phenyl, which is unsubstituted or substituted by one to three substituents selected from halogen and fluoro $(C_1$–$C_6)$-alkyl;
$R^2$ is hydrogen, halogen or $C_1$–$C_6$-alkyl;
$R^3$ is hydrogen, $C_1$–$C_6$-alkyl, $C_3$–$C_6$-cycloalkyl or benzyl;
$R^4$ is halogen, fluoro$(C_1$–$C_6)$-alkyl, cyano, $C_1$–$C_6$-alkoxy or fluoro$(C_1$–$C_6)$-alkoxy;
$R^5$ and $R^6$ are independently from each other hydrogen or $C_1$–$C_6$-alkyl;
$R^7$ is hydrogen or $C_1$–$C_6$-alkyl;
$R^8$ is hydrogen or $C_1$–$C_6$-alkyl;
m is 1, 2 or 3; and
n is 0, 1 or 2;

or a pharmaceutically acceptable salt thereof.

In another aspect the present invention provides a compound of formula I wherein
$R^1$ is —$(CH_2)_n$—CO—$NR^5R^6$; —$(CH_2)_n$—$COOR^7$; —$(CH_2)_n$—$NR^5R^6$; —$(CH_2)_n$—CN; —$(CH_2)_n$—$OR^8$; or phenyl, which is unsubstituted or substituted by one to three substituents selected from halogen and fluoro $(C_1$–$C_6)$-alkyl;
$R^2$ is hydrogen or $C_1$–$C_6$-alkyl;
$R^3$ is hydrogen, $C_1$–$C_6$-alkyl, $C_3$–$C_6$-cycloalkyl or benzyl;
$R^4$ is halogen, fluoro$(C_1$–$C_6)$-alkyl, cyano, $C_1$–$C_6$-alkoxy or fluoro$(C_1$–$C_6)$-alkoxy;
$R^5$ and $R^6$ are independently from each other hydrogen or $C_1$–$C_6$-alkyl;
$R^7$ is hydrogen or $C_1$–$C_6$-alkyl;
$R^8$ is hydrogen or $C_1$–$C_6$-alkyl;
m is 1, 2 or 3; and
n is 0, 1 or 2;

or a pharmaceutically acceptable salt thereof.

In another aspect, the present invention relates to compositions containing one or more compounds of the invention and a pharmaceutically acceptable carrier. In yet another aspect, the invention relates to a process for the manufacture of compounds of the invention.

Compounds of the present invention are highly selective MAO-B inhibitors. Thus, the present invention also relates to methods for the treatment or prevention of diseases mediated by monoamine oxidase B. Such diseases include, for example, Alzheimer's disease, senile dementia, and Parkinson's disease.

DESCRIPTION OF THE INVENTION

The following definitions of general terms used in the present patent application apply irrespective of whether the terms in question appear alone or in combination. It must be noted that, as used in the specification and the appended claims, the singular forms "a", "an," and "the" include plural forms unless the context clearly dictates otherwise.

The term "$(C_1-C_6)$-alkyl" ("lower alkyl") used in the present application denotes straight-chain or branched saturated hydrocarbon residues with 1 to 6 carbon atoms, preferably with 1 to 4 carbon atoms, such as methyl, ethyl, n-propyl, i-propyl, n-butyl, sec-butyl, t-butyl, and the like.

"$(C_3-C_6)$-Cycloalkyl" means non-aromatic, partially or completely saturated monovalent cyclic hydrocarbon radical containing from 3 to 6 carbon atoms. Examples of cycloalkyl groups include cyclopropyl, cyclobutyl, cyclopentyl, and cyclohexyl.

The term "halogen" denotes fluorine, chlorine, bromine and iodine.

"Halogen-$(C_1-C_6)$-alkyl" or "halogen-$(C_1-C_6)$-alkoxy" means the lower alkyl residue lower alkoxy residue as defined herein substituted in any position with one or more halogen atoms as defined herein. Examples of halogenalkyl residues include, but are not limited to, 1,2-difluoropropyl, 1,2-dichloropropyl, trifluoromethyl, 2,2,2-trifluoroethyl, 2,2,2-trichloroethyl, and 1,1,1-trifluoropropyl, and the like. Halogenalkoxy" includes, but is not limited to, fluoro$(C_1-C_6)$-alkoxy, trifluoromethyloxy, and the like.

"$C_1-C_6$-Alkoxy" means the residue —O—R, wherein R is a lower alkyl residue as defined herein. Examples of alkoxy radicals include, but are not limited to, methoxy, ethoxy, isopropoxy, and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base. It should be understood that all references to pharmaceutically acceptable salts include solvent addition forms (solvates) or crystal forms (polymorphs) of the same acid addition salt.

"Therapeutically effective amount" means an amount that is effective to prevent, alleviate or ameliorate symptoms of disease or prolong the survival of the subject being treated.

The present invention provides a compound of formula I

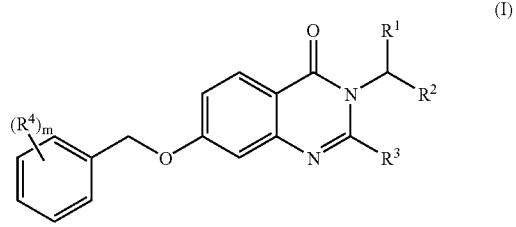

wherein
$R^1$ is —$(CH_2)_n$—CO—$NR^5R^6$; —$(CH_2)_n$—$COOR^7$; —$(CH_2)_n$—$NR^5R^6$; —$(CH_2)_n$—CN; —$(CH_2)_n$—$OR^8$; or phenyl, which is unsubstituted or substituted by one to three substituents selected from halogen and fluoro $(C_1-C_6)$-alkyl;
$R^2$ is hydrogen, halogen or $C_1-C_6$-alkyl;
$R^3$ is hydrogen, $C_1-C_6$-alkyl, $C_3-C_6$-cycloalkyl or benzyl;
$R^4$ is halogen, fluoro$(C_1-C_6)$-alkyl, cyano, $C_1-C_6$-alkoxy or fluoro$(C_1-C_6)$-alkoxy;
$R^5$ and $R^6$ are independently from each other hydrogen or $C_1-C_6$-alkyl;
$R^7$ is hydrogen or $C_1-C_6$-alkyl;
$R^8$ is hydrogen or $C_1-C_6$-alkyl;
m is 1, 2 or 3; and
n is 0, 1 or 2;

or a pharmaceutically acceptable salt thereof.

The present invention further provides a compound of formula I wherein
$R^1$ is —$(CH_2)_n$—CO—$NR^5R^6$; —$(CH_2)_n$—$COOR^7$; —$(CH_2)_n$—$NR^5R^6$; —$(CH_2)_n$—CN; —$(CH_2)_n$—$OR^8$; or phenyl, which is unsubstituted or substituted by one to three substituents selected from halogen and fluoro $(C_1-C_6)$-alkyl;
$R^2$ is hydrogen or $C_1-C_6$-alkyl;
$R^3$ is hydrogen, $C_1-C_6$-alkyl, $C_3-C_6$-cycloalkyl or benzyl;
$R^4$ is halogen, fluoro$(C_1-C_6)$-alkyl, cyano, $C_1-C_6$-alkoxy or fluoro$(C_1-C_6)$-alkoxy;
$R^5$ and $R^6$ are independently from each other hydrogen or $C_1-C_6$-alkyl;
$R^7$ is hydrogen or $C_1-C_6$-alkyl;
$R^8$ is hydrogen or $C_1-C_6$-alkyl;
m is 1, 2 or 3; and
n is 0, 1 or 2;

or a pharmaceutically acceptable salt thereof.

The present invention also provides a compound of formula I wherein
$R^1$ is —$(CH_2)_n$—CO—$NR^5R^6$; —$(CH_2)_n$—$COOR^7$; —$(CH_2)_n$—$NR^5R^6$; —$(CH_2)_n$—CN; —$(CH_2)_n$—$OR^8$; or phenyl, which is unsubstituted or substituted by one to three substituents selected from halogen and fluoro $(C_1-C_6)$-alkyl;
$R^2$ is halogen or $C_1-C_6$-alkyl;
$R^3$ is hydrogen, $C_1-C_6$-alkyl, $C_3-C_6$-cycloalkyl or benzyl;
$R^4$ is halogen, fluoro$(C_1-C_6)$-alkyl, cyano, $C_1-C_6$-alkoxy or fluoro$(C_1-C_6)$-alkoxy;
$R^5$ and $R^6$ are independently from each other hydrogen or $C_1-C_6$-alkyl;
$R^7$ is hydrogen or $C_1-C_6$-alkyl;
$R^8$ is hydrogen or $C_1-C_6$-alkyl;
m is 1, 2 or 3; and
n is 0, 1 or 2;

or a pharmaceutically acceptable salt thereof.

The present invention provides a compound of formula I wherein
$R^1$ is —$(CH_2)_n$—CO—$NR^5R^6$; —$(CH_2)_n$—$COOR^7$; —$(CH_2)_n$—$NR^5R^6$; —$(CH_2)_n$—CN; —$(CH_2)_n$—$OR^8$; or phenyl, which is unsubstituted or substituted by one to three substituents selected from halogen and fluoro($C_1$–$C_6$)-alkyl;
$R^2$ is hydrogen, halogen or $C_1$–$C_6$-alkyl;
$R^3$ is hydrogen or $C_1$–$C_6$-alkyl,
$R^4$ is halogen, fluoro($C_1$–$C_6$)-alkyl, cyano, $C_1$–$C_6$-alkoxy or fluoro($C_1$–$C_6$)-alkoxy;
$R^5$ and $R^6$ are independently from each other hydrogen or $C_1$–$C_6$-alkyl;
$R^7$ is hydrogen or $C_1$–$C_6$-alkyl;
$R^8$ is hydrogen or $C_1$–$C_6$-alkyl;
m is 1, 2 or 3; and
n is 0, 1 or 2;

or a pharmaceutically acceptable salt thereof.

The present invention also provides a compound of formula I wherein
$R^1$ is —$(CH_2)_n$—CO—$NR^5R^6$; —$(CH_2)_n$—$COOR^7$; —$(CH_2)_n$—$NR^5R^6$; —$(CH_2)_n$—CN; —$(CH_2)_n$—$OR^8$; or phenyl, which is unsubstituted or substituted by one to three substituents selected from halogen and fluoro($C_1$–$C_6$)-alkyl;
$R^2$ is hydrogen, halogen or $C_1$–$C_6$-alkyl;
$R^3$ is $C_3$–$C_6$-cycloalkyl or benzyl;
$R^4$ is halogen, fluoro($C_1$–$C_6$)-alkyl, cyano, $C_1$–$C_6$-alkoxy or fluoro($C_1$–$C_6$)-alkoxy;
$R^5$ and $R^6$ are independently from each other hydrogen or $C_1$–$C_6$-alkyl;
$R^7$ is hydrogen or $C_1$–$C_6$-alkyl;
$R^8$ is hydrogen or $C_1$–$C_6$-alkyl;
m is 1, 2 or 3; and
n is 0, 1 or 2;

or a pharmaceutically acceptable salt thereof.

The present invention further provides a compound of formula I wherein
$R^1$ is —$(CH_2)_n$—CO—$NH_2$; —$(CH_2)_n$—$COOR^7$; —$(CH_2)_n$—$NH_2$; —$(CH_2)_n$—CN; —$(CH_2)_n$—$OR^8$; or phenyl, which is unsubstituted or substituted by one to three substituents selected from halogen and fluoro($C_1$–$C_6$)-alkyl;
$R^2$ is hydrogen, halogen or $C_1$–$C_6$-alkyl;
$R^3$ is hydrogen, $C_1$–$C_6$-alkyl, $C_3$–$C_6$-cycloalkyl or benzyl;
$R^4$ is halogen, fluoro($C_1$–$C_6$)-alkyl, cyano, $C_1$–$C_6$-alkoxy or fluoro($C_1$–$C_6$)-alkoxy;
$R^5$ and $R^6$ are independently from each other hydrogen or $C_1$–$C_6$-alkyl;
$R^7$ is hydrogen or $C_1$–$C_6$-alkyl;
$R^8$ is hydrogen or $C_1$–$C_6$-alkyl;
m is 1, 2 or 3; and
n is 0, 1 or 2;

or a pharmaceutically acceptable salt thereof.

The present invention provides a compound of formula I wherein
$R^1$ is —$(CH_2)_n$—CO—$NR^5R^6$; —$(CH_2)_n$—$COOR^7$; —$(CH_2)_n$—$NR^5R^6$; —$(CH_2)_n$—CN; —$(CH_2)_n$—$OR^8$; or phenyl, which is unsubstituted or substituted by one to three substituents selected from halogen and fluoro($C_1$–$C_6$)-alkyl;
$R^2$ is hydrogen, halogen or $C_1$–$C_6$-alkyl;
$R^3$ is hydrogen, $C_1$–$C_6$-alkyl, $C_3$–$C_6$-cycloalkyl or benzyl;
$R^4$ is halogen, fluoro($C_1$–$C_6$)-alkyl;
$R^5$ and $R^6$ are independently from each other hydrogen or $C_1$–$C_6$-alkyl;
$R^7$ is hydrogen or $C_1$–$C_6$-alkyl;
$R^8$ is hydrogen or $C_1$–$C_6$-alkyl;
m is 1, 2 or 3; and
n is 0, 1 or 2;

or a pharmaceutically acceptable salt thereof.

The present invention also provides a compound of formula I wherein
$R^1$ is —$(CH_2)_n$—CO—$NR^5R^6$; —$(CH_2)_n$—$COOR^7$; —$(CH_2)_n$—$NR^5R^6$; —$(CH_2)_n$—CN; —$(CH_2)_n$—$OR^8$; or phenyl, which is unsubstituted or substituted by one to three substituents selected from halogen and fluoro($C_1$–$C_6$)-alkyl;
$R^2$ is hydrogen, halogen or $C_1$–$C_6$-alkyl;
$R^3$ is hydrogen, $C_1$–$C_6$-alkyl, $C_3$–$C_6$-cycloalkyl or benzyl;
$R^4$ is $C_1$–$C_6$-alkoxy or fluoro($C_1$–$C_6$)-alkoxy;
$R^5$ and $R^6$ are independently from each other hydrogen or $C_1$–$C_6$-alkyl;
$R^7$ is hydrogen or $C_1$–$C_6$-alkyl;
$R^8$ is hydrogen or $C_1$–$C_6$-alkyl;
m is 1, 2 or 3; and
n is 0, 1 or 2;

or a pharmaceutically acceptable salt thereof.

It is understood by those having ordinary skill in the art that the invention encompasses all manner of subgenera containing any combination of the values for $R^1$, $R^2$, $R^3$, $R^4$ and m provided above.

In one embodiment the present invention provides a compound of formula I wherein $R^1$ is —$(CH_2)_n$—CO—$NR^5R^6$, for example, compounds in which $R^1$ is —$(CH_2)_n$—CO—$NH_2$. The following are nonlimiting examples of compounds within this embodiment. Such compounds include those where $R^2$ is hydrogen. Also included are compounds wherein $R^2$ is alkyl, for example, methyl. Other such compounds are those wherein $R^2$ is halogen. Compounds of this embodiment also include compounds in which $R^3$ is hydrogen or $C_1$–$C_6$-alkyl, in combination with any of the $R^2$ described herein. Also included are compounds wherein $R^3$ is $C_3$–$C_6$-cycloalkyl or benzyl in combination with any of the $R^2$ described herein. Further included compounds are those wherein $R^4$ is halogen or fluoro($C_1$–$C_6$)-alkyl. Also included are compounds in which $R^4$ is $C_1$–$C_6$-alkoxy or fluoro($C_1$–$C_6$)-alkoxy. Additional compounds are those in which n is 0 or 1.

In one embodiment the present invention provides a compound of formula I wherein $R^1$ is —$(CH_2)_n$—$COOR^7$; wherein $R^7$ is hydrogen or $C_1$–$C_6$-alkyl; and n is 0, 1 or 2. The following are nonlimiting examples of compounds within this embodiment. Such compounds in this embodiment include compounds wherein $R^7$ is hydrogen. Other compounds in this embodiment are those wherein $R^7$ is $C_1$–$C_6$-alkyl. Compounds wherein $R^2$ is hydrogen are included. Also included are compounds wherein $R^2$ is alkyl, for example, methyl. Other such compounds are those wherein $R^2$ is halogen. Compounds of this embodiment also include compounds in which $R^3$ is hydrogen or $C_1$–$C_6$-alkyl, in combination with any of the $R^2$ described herein. Also included are compounds wherein $R^3$ is $C_3$–$C_6$-cycloalkyl or benzyl in combination with any of the $R^2$ described herein. Further included compounds are those wherein $R^4$ is halogen or fluoro($C_1$–$C_6$)-alkyl. Also included are compounds in which $R^4$ is $C_1$–$C_6$-alkoxy or fluoro($C_1$–$C_6$)-alkoxy. Other compounds within this embodiment are those in which n is 0, for example compounds in which $R^1$ is —$(CH_2)_n$—$COOR^7$, wherein $R^7$ is $C_1$–$C_6$-alkyl, and wherein n is 0.

In one embodiment the present invention provides a compound of formula I wherein $R^1$ is —$(CH_2)_n$—CO—$NR^5R^6$, for example, compounds in which $R^1$ is —$(CH_2)_n$—$NH_2$. The following are nonlimiting examples of compounds within this embodiment. Such compounds include those where $R^2$ is hydrogen. Also included are compounds wherein $R^2$ is alkyl, for example, methyl. Other such compounds are those wherein $R^2$ is halogen. Compounds of this embodiment also include compounds in which $R^3$ is hydrogen or $C_1$–$C_6$-alkyl, in combination with any of the $R^2$ described herein. Also included are compounds wherein $R^3$ is $C_3$–$C_6$-cycloalkyl or benzyl in combination with any of the $R^2$ described herein. Further included compounds are those wherein $R^4$ is halogen or fluoro($C_1$–$C_6$)-alkyl. Also included are compounds in which $R^4$ is $C_1$–$C_6$-alkoxy or fluoro($C_1$–$C_6$)-alkoxy. Additional compounds are those in which n is 0 or 1. Other compounds within this embodiment are those in which n is 1 or 2.

In one embodiment the present invention provides a compound of formula I wherein $R^1$ is —$(CH_2)_n$—CN; and n is 0, 1 or 2. In another embodiment the present invention provides a compound of formula I wherein $R^1$ is —CN. The following are nonlimiting examples of compounds within these embodiments. Compounds in each of these embodiments include those where $R^2$ is hydrogen. Also included are compounds wherein $R^2$ is alkyl, for example, methyl. Other such compounds are those wherein $R^2$ is halogen. Compounds of these embodiments also include compounds in which $R^3$ is hydrogen or $C_1$–$C_6$-alkyl, in combination with any of the $R^2$ described herein. Also included are compounds wherein $R^3$ is $C_3$–$C_6$-cycloalkyl or benzyl in combination with any of the $R^2$ described herein. Further included compounds are those wherein $R^4$ is halogen or fluoro($C_1$–$C_6$)-alkyl. Also included are compounds in which $R^4$ is $C_1$–$C_6$-alkoxy or fluoro($C_1$–$C_6$)-alkoxy.

In one embodiment the present invention provides a compound of formula I wherein $R^1$ is —$(CH_2)_n$—$OR^8$. The following are nonlimiting examples of compounds within these embodiments. Compounds of this embodiment include those in which $R^8$ is hydrogen. Also included are compounds wherein $R^8$ is $C_1$–$C_6$-alkyl. Compounds in each of these embodiments include those where $R^2$ is hydrogen. Also included are compounds wherein $R^2$ is alkyl, for example, methyl. Other such compounds are those wherein $R^2$ is halogen. Compounds of these embodiments also include compounds in which $R^3$ is hydrogen or $C_1$–$C_6$-alkyl, in combination with any of the $R^2$ described herein. Also included are compounds wherein $R^3$ is $C_3$–$C_6$-cycloalkyl or benzyl in combination with any of the $R^2$ described herein. Further included compounds are those wherein $R^4$ is halogen or fluoro($C_1$–$C_6$)-alkyl. Also included are compounds in which $R^4$ is $C_1$–$C_6$-alkoxy or fluoro($C_1$–$C_6$)-alkoxy.

In one embodiment the present invention provides a compound of formula I wherein $R^1$ is or phenyl. Such compounds include those wherein the phenyl group is unsubstituted or substituted, for example, by halogen. Compounds of this embodiment in which $R^1$ is substituted phenyl can also be substituted with fluoro($C_1$–$C_6$)-alkyl. The following are nonlimiting examples of compounds within this embodiment. Such compounds include those where $R^2$ is hydrogen. Also included are compounds wherein $R^2$ is alkyl, for example, methyl. Other such compounds are those wherein $R^2$ is halogen. Compounds of this embodiment also include compounds in which $R^3$ is hydrogen or $C_1$–$C_6$-alkyl, in combination with any of the $R^2$ described herein. Also included are compounds wherein $R^3$ is $C_3$–$C_6$-cycloalkyl or benzyl in combination with any of the $R^2$ described herein.

Further included compounds are those wherein $R^4$ is halogen or fluoro($C_1$–$C_6$)-alkyl. Also included are compounds in which $R^4$ is $C_1$–$C_6$-alkoxy or fluoro($C_1$–$C_6$)-alkoxy.

In one embodiment the present invention provides a compound of formula I wherein $R^2$ is hydrogen or $C_1$–$C_6$-alkyl. In another embodiment the present invention provides a compound of formula I wherein $R^2$ is hydrogen or methyl. Within each of these embodiments, any combination of $R^1$, $R^3$, and $R^4$ is contemplated.

In one embodiment the present invention provides a compound of formula I wherein $R^3$ is $C_1$–$C_6$-alkyl, $C_3$–$C_6$-cycloalkyl or benzyl. In another embodiment the present invention provides a compound of formula I wherein $R^3$ is $C_3$–$C_6$-cycloalkyl. In another embodiment the present invention provides a compound of formula I wherein $R^3$ is benzyl. In another embodiment, the present invention provides a compound of formula I wherein $R^3$ is $C_1$–$C_6$-alkyl. Within each of these embodiments, any combination of $R^1$, $R^2$, and $R^4$ is contemplated.

In one embodiment the present invention provides a compound of formula I wherein $R^4$ is halogen; for example, compounds where $R^4$ is a halogen, and m is 1. In another embodiment, the present invention provides a compound of formula I wherein $R^4$ is fluoro($C_1$–$C_6$)-alkyl. In yet another embodiment the present invention provides a compound of formula I wherein $R^4$ is cyano. In another embodiment, the present invention provides a compound of formula I wherein $R^4$ is $C_1$–$C_6$-alkoxy or fluoro($C_1$–$C_6$)alkoxy. Within each of these embodiment, any combination of $R^1$, $R^2$, and $R^3$ is contemplated.

Among compounds of the present invention certain compounds of formula I, or pharmaceutically acceptable salts thereof, are preferred.

Preferred compounds of formula I are those, wherein $R^3$ is hydrogen.

Also preferred are compounds of formula I, wherein $R^3$ is ($C_1$–$C_6$)-alkyl. Especially preferred are those, wherein $R^3$ is methyl.

Compounds of formula I, wherein $R^3$ is $C_3$–$C_6$-cycloalkyl or benzyl, are also preferred.

Preferred compounds of formula I are further those, wherein $R^1$ is —$(CH_2)_n$—CO—$NR^5R^6$, wherein $R^5$ and $R^6$ are independently from each other hydrogen or $C_1$–$C_6$-alkyl, and n is 0, 1 or 2. Especially preferred are those compounds, wherein $R^5$ and $R^6$ are hydrogen, and n is 0, 1 or 2.

Even more preferred are compounds of formula I, wherein $R^1$ is —$(CH_2)_n$—CO—$NR^5R^6$, wherein $R^5$ and $R^6$ are hydrogen, and n is 0.

The following compounds are examples thereof:

2-[7-(3-fluoro-benzyloxy)-4-oxo-4H-quinazolin-3-yl]-acetamide,

2-[7-(3-fluoro-benzyloxy)-4-oxo-4H-quinazolin-3-yl]-propionamide,

2-[7-(4-fluoro-benzyloxy)-4-oxo-4H-quinazolin-3-yl]-acetamide,

2-[7-(4-fluoro-benzyloxy)-4-oxo-4H-quinazolin-3-yl]-propionamide,

2-[7-(3-fluoro-benzyloxy)-2-methyl-4-oxo-4H-quinazolin-3-yl]-acetamide, and

2-[2-cyclopropyl-7-(3-fluoro-benzyloxy)-4-oxo-4H-quinazolin-3-yl]-acetamide.

Also preferred are compounds of formula I, wherein $R^1$ is —$(CH_2)_n$—$OR^8$, wherein $R^8$ is hydrogen or $C_1$–$C_6$-alkyl, and n is 0, 1 or 2. Especially preferred are those compounds, wherein $R^8$ is methyl and n is 1.

Examples thereof are the following compounds:
7-(3-fluoro-benzyloxy)-3-(2-methoxy-ethyl)-3H-quinazolin-4-one,
7-(4-fluoro-benzyloxy)-3-(2-methoxy-ethyl)-3H-quinazolin-4-one, and
7-(3-fluoro-benzyloxy)-3-(2-methoxy-ethyl)-2-methyl-3H-quinazolin-4-one.

Further preferred are compounds of formula I, wherein $R^1$ is —$(CH_2)_n$—$NR^5R^6$, wherein $R^5$ and $R^6$ are independently from each other hydrogen or $C_1$–$C_6$-alkyl, and n is 0, 1 or 2.

Especially preferred within this group of compounds are those, wherein $R^5$ and $R^6$ are hydrogen, and n is 0, 1 or 2.

The following compounds are examples thereof:
3-(2-amino-ethyl)-7-(3-fluoro-benzyloxy)-3H-quinazolin-4-one 1:2 hydrochloride,
3-(3-amino-propyl)-7-(3-fluoro-benzyloxy)-3H-quinazolin-4-one 1:2 hydrochloride,
3-(2-amino-ethyl)-7-(4-fluoro-benzyloxy)-3H-quinazolin-4-one 1:1 hydrochloride, and
2-[7-(3-fluoro-benzyloxy)-2-methyl-4-oxo-4H-quinazolin-3-yl]-ethyl-ammonium chloride.

Preferred compounds of formula I are especially those, wherein $R^4$ is halogen or fluoro($C_1$–$C_6$)-alkyl. More preferably, $R^4$ is fluoro.

In another embodiment the present invention provides a compound of formula I selected from
2-[7-(3-fluoro-benzyloxy)-4-oxo-4H-quinazolin-3-yl]-acetamide,
2-[7-(3-fluoro-benzyloxy)-4-oxo-4H-quinazolin-3-yl]-propionamide,
2-[7-(4-fluoro-benzyloxy)-4-oxo-4H-quinazolin-3-yl]-acetamide,
2-[7-(4-fluoro-benzyloxy)-4-oxo-4H-quinazolin-3-yl]-propionamide,
2-[7-(3-fluoro-benzyloxy)-2-methyl-4-oxo-4H-quinazolin-3-yl]-acetamide,
2-[2-cyclopropyl-7-(3-fluoro-benzyloxy)-4-oxo-4H-quinazolin-3-yl]-acetamide,
7-(3-fluoro-benzyloxy)-3-(2-methoxy-ethyl)-3H-quinazolin-4-one,
7-(4-fluoro-benzyloxy)-3-(2-methoxy-ethyl)-3H-quinazolin-4-one,
7-(3-fluoro-benzyloxy)-3-(2-methoxy-ethyl)-2-methyl-3H-quinazolin-4-one,
3-(2-amino-ethyl)-7-(3-fluoro-benzyloxy)-3H-quinazolin-4-one 1:2 hydrochloride,
3-(3-amino-propyl)-7-(3-fluoro-benzyloxy)-3H-quinazolin-4-one 1:2 hydrochloride,
3-(2-amino-ethyl)-7-(4-fluoro-benzyloxy)-3H-quinazolin-4-one 1:1 hydrochloride, and
2-[7-(3-fluoro-benzyloxy)-2-methyl-4-oxo-4H-quinazolin-3-yl]-ethyl-ammonium chloride.

In a further aspect the present invention provides a process for the preparation of a compound of formula I and a pharmaceutically acceptable salt thereof comprising reacting a compound of formula IV

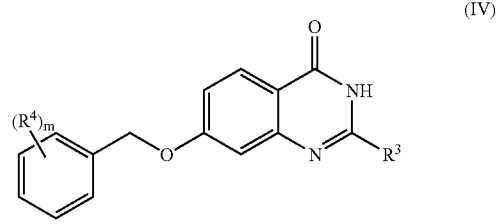

(IV)

wherein
$R^3$ is hydrogen, $C_1$–$C_6$-alkyl, $C_3$–$C_6$-cycloalkyl or benzyl;
$R^4$ is halogen, fluoro($C_1$–$C_6$)-alkyl, cyano, $C_1$–$C_6$-alkoxy or fluoro($C_1$–$C_6$)-alkoxy; and
m is 1, 2 or 3 with a compound of formula V

(V)

wherein
$R^1$ is —$(CH_2)_n$—CO—$NR^5R^6$; —$(CH_2)_n$—$COOR^7$; —$(CH_2)_n$—$NR^5R^6$; —$(CH_2)_n$—CN; —$(CH_2)_n$—$OR^8$; or phenyl, which is unsubstituted or substituted by one to three substituents selected from halogen and fluoro ($C_1$–$C_6$)-alkyl;
$R^2$ is hydrogen, halogen or $C_1$–$C_6$-alkyl;
$R^5$ and $R^6$ are independently from each other hydrogen or $C_1$–$C_6$-alkyl;
$R^7$ is hydrogen or $C_1$–$C_6$-alkyl;
$R^8$ is hydrogen or $C_1$–$C_6$-alkyl; and
n is 0, 1 or 2;

and optionally converting the resulting compound of formula I into a pharmaceutically acceptable salt.

In one embodiment the compounds of general formula I and their pharmaceutically acceptable salts can be manufactured by reacting a compound of formula II

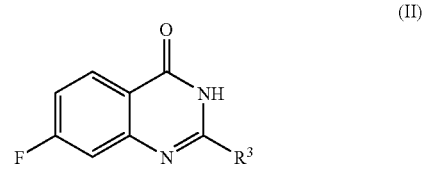

(II)

wherein $R^3$ is hydrogen, with a compound of formula III

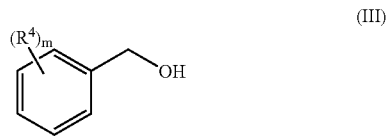

(III)

to obtain a compound of formula IV

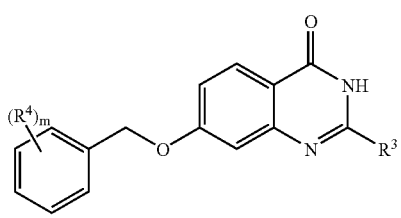

wherein R³ is hydrogen, which in turn is reacted with a compound of formula V

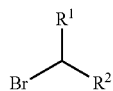

to obtain a compound of formula I and, if desired, converting a compound of formula I into a pharmaceutically acceptable salt, or alternatively, reacting a compound of formula VI

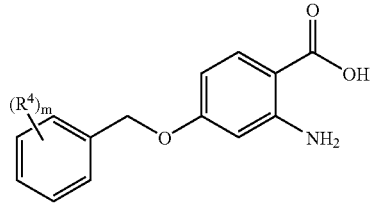

with a compound of formula VII

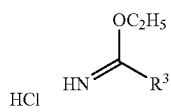

to obtain a compound of formula IV which in turn is reacted with a compound of formula V to obtain a compound of formula I and, if desired, converting a compound of formula I into a pharmaceutically acceptable salt.

In accordance with the present invention, compounds of general formula I can be prepared following scheme 1: 2-Amino-4-fluorobenzoic acid VIII is heated in the presence of formamidine acetate IX which after basification of the reaction medium affords compounds of type IIa. Subsequent reaction with the sodium salts of benzylic alcohols of type X affords compounds of type IVa which are then dissolved in 1-methyl-2-pyrrolidone (NMP) and treated with sodium hydride and an electrophile of formula V to give compounds of formula I, wherein R³ is hydrogen.

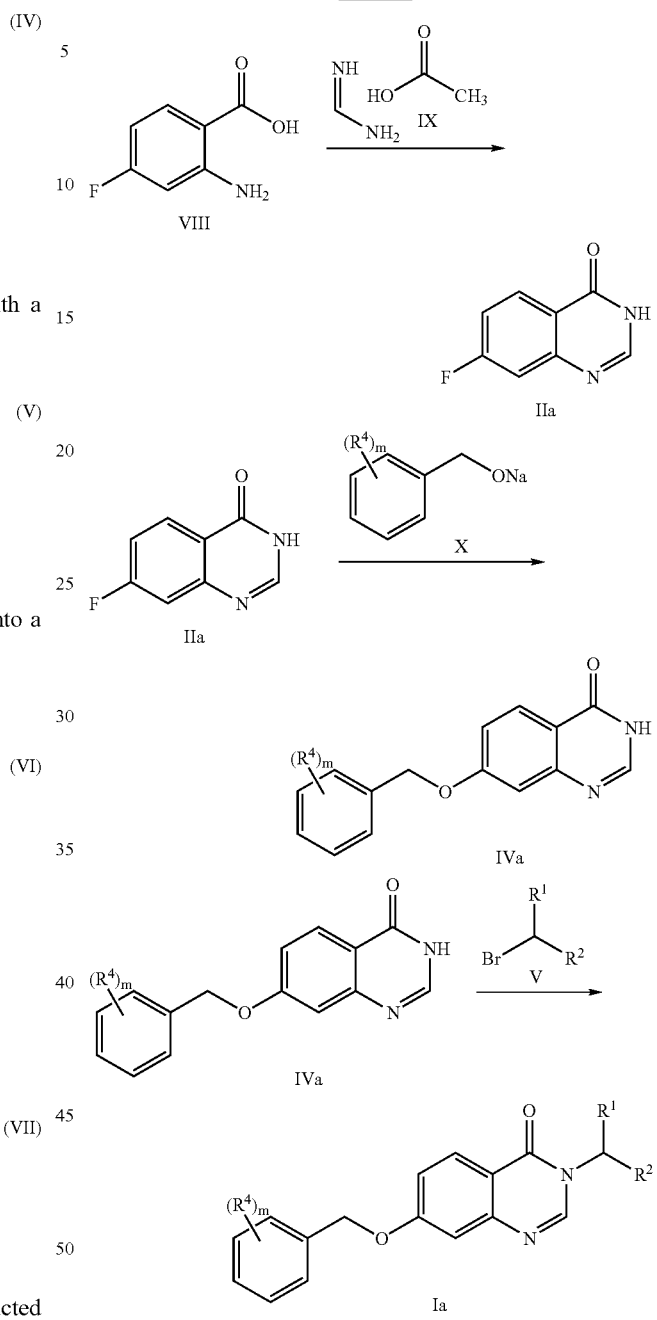

Alternatively, compounds of general formula I can be prepared according to the following scheme 2: 4-Fluoro-2-nitro-benzonitrile XI is heated in the presence of HBr and the resulting acid XII is esterified with acidic methanol to afford a compound of formula XIII. Subsequent reaction with the sodium salts of benzylic alcohols of type X affords compounds of type XIV, which are then hydrogenated to anilines of formula VI. Treatment with acetamidate hydrochloride of type VII in base (usually sodium methoxide) forms the quinazolinones IV which are then alkylated with compounds of type V to form the target compounds of formula I.

Scheme 2

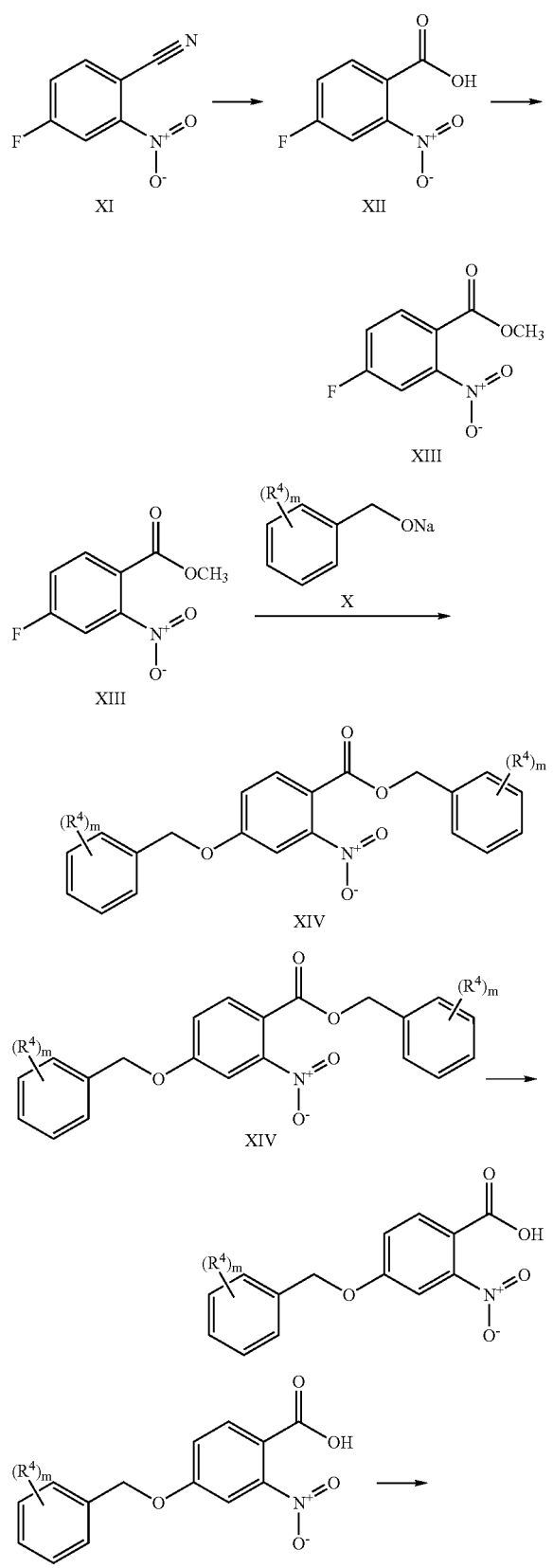

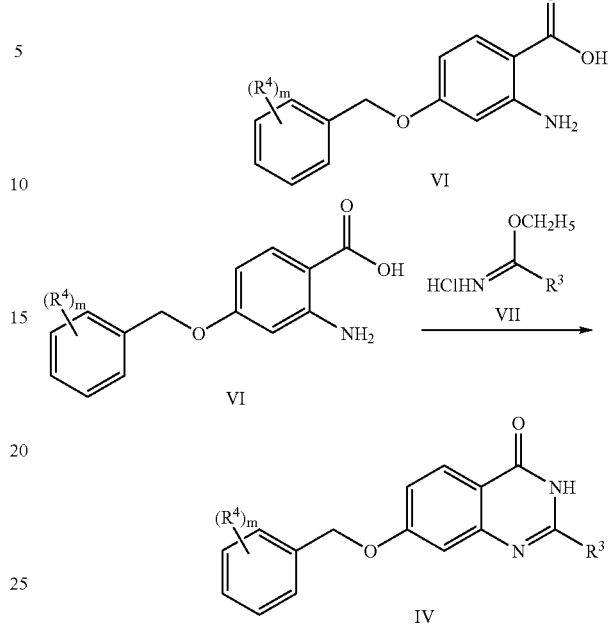

All starting materials employed in the processes described herein are either commercially available or can be prepared by conventional means.

Pharmaceutically acceptable salts of compounds of formula I can be manufactured readily according to methods known per se and taking into consideration the nature of the compound to be converted into a salt. Inorganic or organic acids such as, e.g., hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, monoamine oxidase B inhibitors and can be used for the treatment or prevention of diseases in which MAO-B inhibitors might be beneficial. These include acute and chronic neurological disorders, cognitive disorders and memory deficits. Treatable neurological disorders are for instance traumatic or chronic degenerative processes of the nervous system, such as Alzheimer's disease, other types of dementia, minimal cognitive impairment or Parkinson's disease. Other indications include psychiatric diseases such as depression, anxiety, panic attack, social phobia, schizophrenia, eating and metabolic disorders such as obesity as well as the prevention and treatment of withdrawal syndromes induced by abuse of alcohol, nicotine and other addictive drugs. Other treatable indications maybe reward deficiency syndrome (WO 01/34172), peripheral neuropathy caused by cancer chemotherapy (WO 97/33572), or the treatment of multiple sclerosis (WO 96/40095) and other neuroinflammatory diseases.

The pharmacological activity of the compounds was tested using the following method:

The cDNA's encoding human MAO-A and MAO-B were transiently transfected into EBNA cells using the procedure described by Schlaeger and Christensen [Cytotechnology, 15:1–13 (1998)]. After transfection, cells were homogeneised by means of a Polytron homogeneiser in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing step with 20 mM Tris HCl buffer, pH 8.0, containing 0.5 mM EGTA, membranes were eventually re-suspended in the above buffer and aliquots stored at −80° C. until use.

MAO-A and MAO-B enzymatic activity was assayed in 96-well-plates using a spectrophotometric assay adapted from the method described by Zhou and PanchukVoloshina [Analytical Biochemistry 253:169–174 (1997)]. Briefly, membrane aliquots were incubated in 0.1 M potassium phosphate buffer, pH 7.4, for 30 min at 37° C. with or without various concentrations of the compounds. After this period, the enzymatic reaction was started by the addition of the MAO substrate tyramine together with 1 U/ml horseradish peroxidase (Roche Biochemicals) and 80 μM N-acetyl-3,7,-dihydroxyphenoxazine (Amplex Red, Molecular Probes). The samples were further incubated for 30 min at 37° C. in a final volume of 200 μl and absorbance was then determined at a wavelength of 570 nm using a SpectraMax plate reader (Molecular Devices). Background (non-specific) absorbance was determined in the presence of 10 μM clorgyline for MAO-A or 10 μM L-deprenyl for MAO-B. $IC_{50}$ values were determined from inhibition curves obtained using nine inhibitor concentrations in duplicate, by fitting data to a four parameter logistic equation using a computer program.

The compounds of the present invention are specific MAO-B inhibitors. The activities of compounds of formula I as measured in the assay described above are in the range of 10 μM or less, typically of 1 μM or less, and ideally 0.3 μM or less.

The present invention also provides pharmaceutical compositions containing compounds of formula I or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injection solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, e.g., as such carriers for tablets, coated tablets, dragées and hard gelatine capsules. Suitable carriers for soft gelatine capsules are, e.g., vegetable oils, waxes, fats, semi-solid and liquid polyols and the like; depending on the nature of the active substance no carriers are, however, usually required in the case of soft gelatine capsules. Suitable carriers for the production of solutions and syrups are, e.g., water, polyols, sucrose, invert sugar, glucose and the like. Adjuvants, such as alcohols, polyols, glycerol, vegetable oils and the like, can be used for aqueous injection solutions of water-soluble salts of compounds of the invention, but as a rule are not necessary. Suitable carriers for suppositories are, e.g., natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions or suspensions. The pharmaceutical compositions also can be administered rectally, for example, in the form of suppositories or parenterally, for example, in the form of injection solutions.

Compounds of the present invention are selective MAO-B inhibitors. Therefore, the present invention also provides methods of treating diseases that are mediated by monoamine oxidase B. For example, the invention provides a method of treating Alzheimer's disease in an individual which comprises administering to the individual an effective amount of a compound of the invention. The invention also provides a method of treating senile dementia in an individual which comprises administering to the individual an effective amount of a compound of the invention. The invention further provides a method of treating Parkinson's disease in an individual which comprises administering to the individual an effective amount of a compound of the invention.

The dosage at which the compounds/compositions are administered can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The following examples are provided for illustration of the invention. They should not be considered as limiting the scope of the invention, but merely as being representative thereof. The term "room temperature" is abbreviated as "rt".

EXAMPLE 1

2-[7-(3-Fluoro-benzyloxy)-4-oxo-4H-quinazolin-3-yl]-acetamide a) 7-Fluoro-3H-quinazolin-4-one: A mixture of 2-amino-4-fluorobenzoic acid (14.6 g, 94 mmol) and formamidine acetate (19.6 g, 18.8 mmol) in 2-methoxyethanol (110 mL) was heated at 130° C. for 18 h. After cooling, the mixture was half evaporated and an off-white solid formed. The mixture was diluted with ammonia (25%, 10 mL in 90 mL water) and the solid filtered off and washed with water. The solid was then washed with hexane and dried under high vacuum to afford the title compound (12.5 g, 81%) as an off-white solid. MS: m/e=165.2 (M+H$^+$).

b) 7-(3-Fluoro-benzyloxy)-3H-quinazolin-4-one: Sodium (1.8 g, 78.6 mmol) was added portionwise to 3-fluorobenzyl alcohol and the resulting mixture heated at 80–90° C. for 4 h under Argon. The resulting suspension was cooled to rt and 7-fluoro-3H-quinazolin-4-one (3.2 g, 19.5 mmol) was added and the resulting mixture heated at 130–140° C. for 14 h. The solid formed was then dissolved with water (400 mL) and the mixture acidified to pH 3–4 with HCl (4 N). The resulting precipitate was then filtered off, washed with water (100 mL) and diethylether (100 mL). Recrystallisation from tetrahydrofuran: ethylacetate (1:1) afforded the title compound (3.2 g, 61%) as white crystals. MS: m/e=271.3 (M+H$^+$).

c) 2-[7-(3-Fluoro-benzyloxy)-4-oxo-4H-quinazolin-3-yl]-acetamide: A mixture of 7-(3-fluoro-benzyloxy)-3H-quinazolin-4-one (200 mg, 0.74 mmol) and sodium hydride (55%, 36 mg, 0.81 mmol) in N-methylpyrolidinone (5 mL) was heated at 60° C. for 1 h. Then bromacetamide (117 mg, 0.85 mmol) was added and the resulting mixture was heated at 80° C. for 1 h. After cooling to rt, water (50 mL) was added and the resulting precipitate was washed with methanol and diethylether and then dried under high vacuum to afford the title compound (200 mg, 83%) as an off-white solid. MS: m/e=328.3 (M+H$^+$).

EXAMPLE 2

2-[7-(3-Fluoro-benzyloxy)-4-oxo-4H-quinazolin-3-yl]-propionamide

As described for Example 1c, 7-(3-fluoro-benzyloxy)-3H-quinazolin-4-one (200 mg, 0.74 mmol) was converted to the title compound (190 mg, 75%) (using 2-brompropionamide instead of bromacetamide) which was obtained as a white solid. MS: m/e=342.3 (M+H$^+$).

EXAMPLE 3

7-(3-Fluoro-benzyloxy)-3-(2-methoxy-ethyl)-3H-quinazolin-4-one

As described for Example 1c, 7-(3-fluoro-benzyloxy)-3H-quinazolin-4-one (200 mg, 0.74 mmol) was converted to the title compound (165 mg, 68%) [using (2-bromomethyl)-methylether instead of bromacetamide] which was obtained as a white solid after crystallisation from diethylether: heptane. MS: m/e=342.3 (M+H$^+$).

EXAMPLE 4

3-(2-Amino-ethyl)-7-(3-fluoro-benzyloxy)-3H-quinazolin-4-one 1:2 hydrochloride a) 2-[7-(3-Fluoro-benzyloxy)-4-oxo-4H-quinazolin-3-yl]-ethyl}-carbamic acid tert-butyl ester: As described for Example 1c, 7-(3-fluoro-benzyloxy)-3H-quinazolin-4-one (200 mg, 0.74 mmol) was converted to the title compound (175 mg, 57%) [using 2-(Bocamino)-ethylbromide instead of bromacetamide] which was obtained as a white solid after crystallisation from diethylether: heptane. MS: m/e=342.3 (M+H$^+$).

b) 3-(2-Amino-ethyl)-7-(3-fluoro-benzyloxy)-3H-quinazolin-4-one 1:2 hydrochloride: A mixture of {2-[7-(3-fluoro-benzyloxy)-4-oxo-4H-quinazolin-3-yl] ethyl}-carbamic acid tert-butyl ester (150 mg, 0.36 mmol) and HCl in dioxane (4 N, 3 mL) was stirred at rt for 72 h. The precipitate was filtered off and washed with diethylether to afford the title compound (120 mg, 86%) as a white solid. MS: m/e=314.3 (M+H$^+$).

EXAMPLE 5

[7-(3-Fluoro-benzyloxy)-4-oxo-4H-quinazolin-3-yl]-acetic acid ethyl ester

As described for Example 1c, 7-(3-fluoro-benzyloxy)-3H-quinazolin-4-one (200 mg, 0.74 mmol) was converted to the title compound (170 mg, 65%) [using ethyl bromoacetate instead of bromacetamide] which was obtained as a white solid. MS: m/e=357.3 (M+H$^+$).

EXAMPLE 6

Fluoro-[7-(3-fluoro-benzyloxy)-4-oxo-4H-quinazolin-3-yl]-acetic acid ethyl ester As described for Example 1c, 7-(3-fluoro-benzyloxy)-3H-quinazolin-4-one (200 mg, 0.74 mmol) was converted to the title compound (100 mg, 36%) [using ethyl bromofluoro-acetate instead of bromacetamide] which was obtained as a white solid after purification by chromatography (SiO$_2$, CH$_2$Cl$_2$:2N NH$_3$/MeOH 99:1 to 9:1) and crystallisation from diethylether: heptane. MS: m/e=375.4 (M+H$^+$).

EXAMPLE 7

2-[7-(3-Fluoro-benzyloxy)-4-oxo-4H-quinazolin-3-yl]-propionic acid ethyl ester

As described for Example 1c, 7-(3-fluoro-benzyloxy)-3H-quinazolin-4-one (200 mg, 0.74 mmol) was converted to the title compound (240 mg, 88%) [using ethyl 2-bromo propionate instead of bromacetamide] which was obtained as a colourless oil after purification by chromatography (SiO$_2$, CH$_2$Cl$_2$:2N NH$_3$/MeOH 99:1 to 9:1). MS: m/e=371.3 (M+H$^+$).

EXAMPLE 8

[7-(3-Fluoro-benzyloxy)-4-oxo-4H-quinazolin-3-yl]-acetic acid tert-butyl ester

As described for Example 1c, 7-(3-fluoro-benzyloxy)-3H-quinazolin-4-one (200 mg, 0.74 mmol) was converted to the title compound (277 mg, 97%) [using tert-butylbromacetate instead of bromacetamide] which was obtained as a white solid after purification by chromatography (SiO$_2$, CH$_2$Cl$_2$:2N NH$_3$/MeOH 99:1 to 9:1). MS: m/e=385.3 (M+H$^+$).

EXAMPLE 9

2-[7-(3-Fluoro-benzyloxy)-4-oxo-4H-quinazolin-3-yl]-propionic acid tert-butyl ester As described for Example 1c, 7-(3-fluoro-benzyloxy)-3H-quinazolin-4-one (200 mg, 0.74 mmol) was converted to the title compound (245 mg, 83%) [using 2-bromopropionic acid tert-butyl ester instead of bromacetamide] which was obtained as a white solid after purification by chromatography (SiO$_2$, CH$_2$Cl$_2$:2N NH$_3$/MeOH 99:1 to 9:1). MS: m/e=385.3 (M+H$^+$).

EXAMPLE 10

3-(3-Amino-propyl)-7-(3-fluoro-benzyloxy)-3H-quinazolin-4-one 1:2 hydrochloride a) {3-[7-(3-Fluoro-benzyloxy)-4-oxo-4H-quinazolin-3-yl]-propyl}-carbamic acid tert-butyl ester: As described for Example 1c, 7-(3-fluoro-benzyloxy)-3H-quinazolin-4-one (200 mg, 0.74 mmol) was converted to the title compound (312 mg, 99%) [using 3-(Bocamino)propyl-bromide instead of bromacetamide] which was obtained as a white solid after purification by chromatography (SiO$_2$, CH$_2$Cl$_2$:2N NH$_3$/MeOH 99:1 to 9:1). MS: m/e=428.5 (M+H$^+$).

b) 3-(3-Amino-propyl)-7-(3-fluoro-benzyloxy)-3H-quinazolin-4-one 1:2 hydrochloride: A mixture of {3-[7-(3-fluoro-benzyloxy)-4-oxo-4H-quinazolin-3-yl]-propyl}-carbamic acid tert-butyl ester (275 mg, 0.64 mmol) and HCl in dioxane (4 N, 8 mL) was stirred at rt for 16 h. The precipitate was filtered off and recrystallised from EtOH:ether to afford the title compound (120 mg, 47%) as a white solid. MS: m/e=328.3 (M+H$^+$).

EXAMPLE 11

3-(3-Fluoro-benzyl)-7-(3-fluoro-benzyloxy)-3H-quinazolin-4-one

As described for Example 1c, 7-(3-fluoro-benzyloxy)-3H-quinazolin-4-one (200 mg, 0.74 mmol) was converted to the title compound (253 mg, 90%) [using 3-fluorobenzyl bromide instead of bromacetamide] which was obtained as a white solid after purification by chromatography (SiO$_2$, CH$_2$Cl$_2$:2N NH$_3$/MeOH 99:1 to 9:1). MS: m/e=379.3 (M+H$^+$).

EXAMPLE 12

2-[7-(4-Fluoro-benzyloxy)-4-oxo-4H-quinazolin-3-yl]-acetamide a) 7-(4-Fluoro-benzyloxy)-3H-quinazolin-4-one: A mixture of sodium hydride (55%, 3.2 g, 73 mmol), 4-fluorobenzyl alcohol (9.2 g, 73 mmol) and 7-fluoro-3H-quinazolin-4-one (3.0 g, 18 mmol) in DMF (75 mL) was heated at 140° C. for 2 h. The resulting suspension was cooled to rt and the mixture acidified to pH 3 with HCl (conc.). The resulting precipitate was then filtered off, washed with water and diethylether. Partial purification by chromatography on silica gel eluting with ethyl acetate:hexane (2:1) afforded the title compound (3.2 g, 66%) as an off-white solid. MS: m/e=271.3 (M+H$^+$).

b) 2-[7-(4-Fluoro-benzyloxy)-4-oxo-4H-quinazolin-3-yl]-acetamide: As described for Example 1c, 7-(4-fluoro-benzyloxy)-3H-quinazolin-4-one (Example 12a, 200 mg, 0.74 mmol) was converted to the tide compound (20 mg, 8%) %) which was obtained as a white solid after purification by HPLC (Waters Xterra RP18 (5 μm×50×9 mm) eluting with AcCN/0.1% TFA/Water. MS: m/e=328.3 (M+H$^+$).

EXAMPLE 13

2-[7-(4-Fluoro-benzyloxy)-4-oxo-4H-quinazolin-3-yl]-propionamide

As described for Example 1c, 7-(4-fluoro-benzyloxy)-3H-quinazolin-4-one (400 mg, 1.5 mmol) was converted to the title compound (37 mg, 7%) (using 2-bromopropionamide instead of bromacetamide) which was obtained as a white solid after purification by HPLC (Waters Xterra RP18 (5 μm×50×19 mm) eluting with AcCN/0.1% TFA/Water. MS: m/e=340.2 (M+H$^+$).

EXAMPLE 14

[7-(4-Fluoro-benzyloxy)-4-oxo-4H-quinazolin-3-yl]-acetic acid ethyl ester

As described for Example 1c, 7-(4-fluoro-benzyloxy)-3H-quinazolin-4-one (400 mg, 1.5 mmol) was converted to the title compound (83 mg, 16%) (using ethyl bromoacetate instead of bromacetamide) which was obtained as a white solid after purification by HPLC (Waters Xterra RP18 (5 μm×50×19 mm) eluting with AcCN/0.1% TFA/Water. MS: m/e=357.3 (M+H$^+$).

EXAMPLE 15

2-[7-(4-Fluoro-benzyloxy)-4-oxo-4H-quinazolin-3-yl]-propionic acid ethyl ester

As described for Example 1c, 7-(4-fluoro-benzyloxy)-3H-quinazolin-4-one (400 mg, 1.5 mmol) was converted to the title compound (32 mg, 6%) (using ethyl-2-bromopropionate instead of bromacetamide) which was obtained as a white solid after purification by HPLC (Waters Xterra RP18 (5 μm×50×19 mm) eluting with AcCN/0.1% TFA/Water. MS: m/e=371.3 (M+H$^+$).

EXAMPLE 16

7-(4-Fluoro-benzyloxy)-3-(2-methoxy-ethyl)-3H-quinazolin-4-one

As described for Example 3,7-(4-fluoro-benzyloxy)-3H-quinazolin-4-one (400 mg, 1.5 mmol) was converted to the title compound (115 mg, 24%) which was obtained as a white solid after purification by HPLC (Waters Xterra RP18 (5 μm×50×19 mm) eluting with AcCN/0.1% TFA/Water. MS: m/e=329.1 (M+H$^+$).

EXAMPLE 17

3-(2-Amino-ethyl)-7-(4-fluoro-benzyloxy)-3H-quinazolin-4-one 1:1 hydrochloride a) {2-[7-(4-Fluoro-benzyloxy)-4-oxo-4H-quinazolin-3-yl]-ethyl}-carbamic acid tert-butyl ester: As described for Example 10a, 7-(4-fluoro-benzyloxy)-3H-quinazolin-4-one (300 mg, 1.1 mmol) was converted to the title compound (105 mg, 23%) which was obtained as a white solid after purification by HPLC (Waters Xterra RP18 (5 μm×50×19 mm) eluting with AcCN/0.1% TFA/Water. MS: m/e=414.5 (M+H$^+$).

b) 3-(2-Amino-ethyl)-7-(4-fluoro-benzyloxy)-3H-quinazolin-4-one 1:1 hydrochloride: As described for Example 10b, {2-[7-(4-fluoro-benzyloxy)-4-oxo-4H-quinazolin-3-yl]-ethyl}-carbamic acid tert-butyl ester (102 mg, 0.25 mmol) was converted to the title compound (84 mg, 97%) which was obtained as a white solid. MS: m/e=314.2 (M+H$^+$).

EXAMPLE 18

3-[7-(4-Fluoro-benzyloxy)-4-oxo-4H-quinazolin-3-yl]-propionamide

As described for Example 1c, 7-(4-fluoro-benzyloxy)-3H-quinazolin-4-one (300 mg, 1.1 mmol) was converted to the title compound (72 mg, 19%) (using 3-bromopropionamide instead of bromoacetamide) which was obtained as a white solid after purification by HPLC (Waters Xterra RP18 (5 μm×50×19 mm) eluting with AcCN/0.1% TFA/Water. MS: m/e=342.1 (M+H$^+$).

EXAMPLE 19

2-[7-(3-Fluoro-benzyloxy)-2-methyl-4-oxo-4H-quinazolin-3-yl]-acetamide a) 4-Fluoro-2-nitro-benzoic acid: A mixture of 4-fluoro-2-nitro-benzonitrile (12.2 g, 73.7 mmol) suspended in HBr (48%, 74.5 mL, 664 mmol) was heated at 130° C. for 6.5 h. After cooling to rt water (1 L) was added and the resulting precipitate was washed with water and hexane to afford the title compound (11.0 g, 81%) as a light brown solid. MS: m/e=183.9 (M–H).

b) 4-Fluoro-2-nitro-benzoic acid methyl ester: A mixture of 4-fluoro-2-nitro-benzoic acid (10.9 g, 58.8 mmol) in methanol (120 mL) containing sulfuric acid (1.8 g, 18.7 mmol) was heated under reflux for 41 h. After cooling to rt the mixture was poured into sodium hydrogen carbonate (sat. 250 mL), and extracted with ethyl acetate (3×100 mL). The combined extracts were washed with brine (100 mL) dried and evaporated to leave the title compound (10.7 g, 91%) as a light brown liquid. MS: m/e=199.0 (M–H).

c) 4-(3-Fluoro-benzyloxy)-2-nitro-benzoic acid (3-fluoro-benzyl) ester and 4-(3-fluoro-benzyloxy)-2-nitro-benzoic acid methyl ester: A mixture of 4-fluoro-2-nitro-benzoic acid methyl ester (9.2 g, 46.3 mmol), 3-fluorobenzyl alcohol (16.7 g, 132.4 mmol) and potassium carbonate (12.8 g, 92.6 mmol) in DMF (210 mL) was heated at 65° C. for 48 h. After cooling to rt, the mixture was poured into water (400 mL), and extracted with diethyl ether (3×100 mL). The combined extracts were washed with brine (100 mL) dried and evaporated. Purification by chromatography on silica gel eluting with ethyl acetate:hexane (1:1) afforded the title compound (14.0 g, 76%) as a light yellow liquid.

d) 4-(3-Fluoro-benzyloxy)-2-nitro-benzoic acid: A mixture of 4-(3-fluorobenzyloxy)-2-nitro-benzoic acid (3-fluoro-benzyl) ester and 4-(3-fluoro-benzyloxy)-2-nitro-benzoic acid methyl ester (14.0 g, 35.0 mmol) in THF (120 mL) and water (120 mL), containing lithium hydroxide monohydrate (2.94 g, 70.1 mmol) was stirred at rt for 48 h. Then the mixture was poured into sodium hydroxide (2 N, 50 mL) and then the mixture extracted with diethyl ether (3×150 mL). The aqueous phase was then adjusted to pH 2 with HCl. Then the mixture was poured into sodium hydroxide (2 N, 50 mL) and the aqueous phase was then adjusted to pH 5.2 with HCl then the mixture extracted with diethyl ether (3×100 mL). The combined extracts were then washed with brine (100 mL) dried and evaporated to afford title compound (6.6 g, 65%) as a light yellow solid. MS: m/e=290.0 (M–H).

e) 2-Amino-4-(3-fluoro-benzyloxy)-benzoic acid: A mixture of 4-(3-fluorobenzyloxy)-2-nitro-benzoic acid (7.2 g, 24.8 mmol) in ethyl acetate (150 mL) in the presence of Pt/C (5%, 1.0 g) was hydrogenated at rt and pressure for 3.5 h. The mixture was then filtered and the filtrate was evaporated. The resulting light brown solid was triturated with dichloromethane (DCM) to afford the title compound (5.2 g, 80%) as an off-white solid. MS: m/e=260.1 (M–H).

Alternatively, a mixture of 4-(3-fluoro-benzyloxy)-2-nitro-benzoic acid (6.6 g, 22.8 mmol) in ethyl acetate (140 mL) in the presence of Pd/C (5%, 1.0 g) was hydrogenated at rt and pressure for 3.5 h. The mixture was then filtered and the filtrate was evaporated. The resulting light brown solid was triturated with DCM to afford the title compound (5.1 g, 87%) as an off-white solid.

f) 7-(3-Fluoro-benzyloxy)-2-methyl-3H-quinazolin-4-one: To a mixture of 2-amino-4-(3-fluoro-benzyloxy)-benzoic acid (2.0 g, 7.7 mmol) and ethyl acetamidate HCl (1.9 g, 15.3 mmol) in methanol (30 mL) was added sodium methoxide (5.4 M, 0.83 g, 15.3 mmol) and the resulting mixture was heated under reflux for 19 h. After this time ethyl acetamidate HCl (1.9 g, 15.3 mmol) and sodium methoxide (5.4 M, 0.83 g, 15.3 mmol) was added and the resulting mixture heated for another 1 h. After cooling to rt the mixture was poured into water (40 mL) and then the resulting precipitate was stirred for 2 h, and filtered off to afford the title compound (2.1 g, 97%) as an off-white solid. MS: m/e=283.1 (M–H).

g) 2-[7-(3-Fluoro-benzyloxy)-2-methyl-4-oxo-4H-quinazolin-3-yl]-acetamide: As described for Example 1c, 7-(3-fluoro-benzyloxy)-2-methyl-3H-quinazolin-4-one (250 mg, 0.88 mmol) was converted to the title compound (218 mg, 73%) which was obtained as a white solid after trituration with dichloromethane (DCM). MS: m/e=342.1 (M+H$^+$).

EXAMPLE 20

7-(3-Fluoro-benzyloxy)-3-(2-methoxy-ethyl)-2-methyl-3H-quinazolin-4-one

As described for Example 3,7-(3-fluoro-benzyloxy)-2-methyl-3H-quinazolin-4-one (250 mg, 0.88 mmol) was converted to the title compound (150 mg, 45%) which was obtained as a white solid after purification by chromatography (SiO$_2$, EtOAc:heptane 1:3 to 2:1). MS: m/e=343.1 (M+H$^+$).

EXAMPLE 21

2-[7-(3-Fluoro-benzyloxy)-2-methyl-4-oxo-4H-quinazolin-3-yl]-ethyl-ammonium chloride a) {2-[7-(3-Fluoro-benzyloxy)-2-methyl-4-oxo-4H-quinazolin-3-yl]-ethyl}-carbamic acid tert-butyl ester: As described for Example 4a, 7-(3-fluoro-benzyloxy)-2-methyl-3H-quinazolin-4-one (250 mg, 0.88 mmol) was converted to the title compound (72 mg, 18%) which was obtained as a white solid after purification by chromatography (SiO$_2$, EtOAc:heptane 1:4 to 2:1). MS: m/e=428.3 (M+H$^+$).

b) 2-[7-(3-Fluoro-benzyloxy)-2-methyl-4-oxo-4H-quinazolin-3-yl]-ethyl-ammonium chloride: As described for Example 4b, {2-[7-(3-fluoro-benzyloxy)-2-methyl-4-oxo-4H-quinazolin-3-yl]-ethyl}-carbamic acid tert-butyl ester (50 mg, 0.12 mmol) was converted to the title compound (45 mg, 85%) which was obtained as a white solid after purification by chromatography (SiO$_2$, EtOAc:heptane 1:4 to 2:1). MS: m/e=328.2 (M+H$^+$).

EXAMPLE 22

2-[7-(3-Fluoro-benzyloxy)-2-isopropyl-4-oxo-4H-quinazolin-3-yl]-acetamide a) 7-(3-Fluoro-benzyloxy)-2-isopropyl-3H-quinazolin-4-one: As described for Example 19f, 2-amino-4-(3-fluoro-benzyloxy)-benzoic acid (1 g, 3.8 mmol) was converted to the title compound (196 mg, 16%) [using ethyl isopropylamidate HCl instead of ethyl acetamidate HCl] which was obtained as a white solid after purification by chromatography (SiO$_2$, dichloromethane:MeOH 95:5 to 85:15). MS: m/e=330.1 (M+NH$_4^+$).

b) 2-[7-(3-Fluoro-benzyloxy)-2-isopropyl-4-oxo-4H-quinazolin-3-yl]-acetamide: As described for Example 1c, 7-(3-fluoro-benzyloxy)-2-isopropyl-3H-quinazolin-4-one (80 mg, 0.26 mmol) was converted to the title compound (84 mg, 89%) which was obtained as a white solid after trituration with dichloromethane. MS: m/e=370.2 (M+H$^+$).

EXAMPLE 23

[7-(3-Fluoro-benzyloxy)-2-isopropyl-4-oxo-4H-quinazolin-3-yl]-acetonitrile

To a mixture of 2-[7-(3-fluoro-benzyloxy)-2-isopropyl-4-oxo-4H-quinazolin-3-yl]-acetamide (50 mg, 0.14 mmol) in dimethylformamide (0.5 mL), dichloromethane (2 mL) was added N-ethyl-N,N-diisopropylamine (26.2 mg, 0.2 mmol) and the resulting mixture cooled to −78° C. Then trifluorosulfonic anhydride (49.6 mg, 0.18 mmol) was added and the reaction mixture allowed to warm up to rt over 30 min. The resulting mixture was then poured into sodium hydrogen carbonate (sat. 5 mL), and the mixture extracted with diethylether (3×5 mL). The combined extracts were then washed with brine, dried and evaporated to leave a light yellow solid. Purification by chromatography (SiO$_2$, EtOAc:heptane 1:1 to 85:15) afforded the title compound (26 mg, 55%) as a white solid. MS: m/e=352.2 (M+H$^+$).

EXAMPLE 24

2-[2-Cyclopropyl-7-(3-fluoro-benzyloxy)-4-oxo-4H-quinazolin-3-yl]-acetamide a) 2-Cyclopropyl-7-(3-fluoro-benzyloxy)-3H-quinazolin-4-one: As described for Example 19f, 2-amino-4-(3-fluoro-benzyloxy)-benzoic acid (1.0 g, 3.8 mmol) was converted to the title compound (607 mg, 49%) [using ethyl cyclopropylamidate HCl instead of ethyl acetamidate HCl] which was obtained as a white solid after trituration with diethylether. MS: m/e=311.2 (M+H$^+$).

b) 2-[2-Cyclopropyl-7-(3-fluoro-benzyloxy)-4-oxo-4H-quinazolin-3-yl]acetamide: As described for Example 1c, 2-cyclopropyl-7-(3-fluoro-benzyloxy)-3H-quinazolin-4-one (80 mg, 0.26 mmol) was converted to the title compound (98 mg, 65%) which was obtained as a white solid after purification by chromatography (SiO$_2$, dichloromethane:MeOH 98:2 to 9:1). MS: m/e=368.1 (M+H$^+$).

EXAMPLE 25

2-Cyclopropyl-7-(3-fluoro-benzyloxy)-3-(2-methoxy-ethyl)-3H-quinazolin-4-one

As described for Example 3,2-cyclopropyl-7-(3-fluoro-benzyloxy)-3H-quinazolin-4-one (150 mg, 0.48 mmol) was converted to the title compound (15 mg, 8%) which was obtained as a white solid after purification by chromatography (SiO$_2$, dichloromethane: MeOH 95:5). MS: m/e=369.2 (M+H$^+$).

EXAMPLE 26

[2-Cyclopropyl-7-(3-fluoro-benzyloxy)-4-oxo-4H-quinazolin-3-yl]-acetic acid methyl ester As described for Example 1c, 2-cyclopropyl-7-(3-fluoro-benzyloxy)-3H-quinazolin-4-one (100 mg, 0.3 mmol) was converted to the title compound (33 mg, 27%) [using methyl bromoacetate instead of bromacetamide] which was obtained as a white solid after purification by chromatography (SiO$_2$, EtOAc:heptane 1:9 to 1:1). MS: m/e=383.3 (M+H$^+$).

EXAMPLE 27

2-[2-Benzyl-7-(3-fluoro-benzyloxy)-4-oxo-4H-quinazolin-3-yl]-acetamide a) 2-Benzyl-7-(3-fluoro-benzyloxy)-3H-quinazolin-4-one: As described for Example 19f, 2-amino-4-(3-fluoro-benzyloxy)-benzoic acid (1.0 g, 3.8 mmol) was converted to the title compound (731 mg, 53%) [using ethyl benzylamidate HCl instead of ethyl acetamidate HCl] which was obtained as a white solid after trituration with diethylether. MS: m/e=361.2 (M+H$^+$).

b) 2-[2-Benzyl-7-(3-fluoro-benzyloxy)-4-oxo-4H-quinazolin-3-yl]-acetamide: As described for Example 1c, 2-benzyl-7-(3-fluoro-benzyloxy)-3H-quinazolin-4-one (150 mg, 0.42 mmol) was converted to the title compound (94 mg, 54%) which was obtained as a white solid after purification by chromatography (SiO$_2$, dichlormethane: MeOH 99:1 to 9:1). MS: m/e=418.2 (M+H$^+$).

EXAMPLE A

Tablets

Tablets of the following composition are produced in a conventional manner:

|  | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets

Tablets of the following composition are produced in a conventional manner:

|  | mg/Tablet |
|---|---|
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules

Capsules of the following composition are produced:

|  | mg/Capsule |
| --- | --- |
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

EXAMPLE D

Injection Solution

An injection solution may have the following composition and is manufactured in usual manner:

| Active substance | 1.0 mg |
| --- | --- |
| 1 N HCl | 20.0 µl |
| acetic acid | 0.5 mg |
| NaCl | 8.0 mg |
| phenol | 10.0 mg |
| 1 N NaOH q.s. ad | pH 5 |
| H$_2$O q.s. ad | 1 ml |

The invention claimed is:

1. A compound of formula I (I)

wherein
R$^1$ is —(CH$_2$)$_n$—CO—NR$^5$R$^6$; —(CH$_2$)$_n$—COOR$^7$; —(CH$_2$)$_n$—CN; —(CH$_2$)$_n$—OR$^8$; or phenyl, which is unsubstituted or substituted by one to three substituents selected from halogen and fluoro(C$_1$–C$_6$)-alkyl;
R$^2$ is hydrogen, halogen or C$_1$–C$_6$-alkyl;
R$^3$ is hydrogen, C$_1$–C$_6$-alkyl, C$_3$–C$_6$-cycloalkyl or benzyl;
R$^4$ is halogen, fluoro(C$_1$–C$_6$)-alkyl, cyano, C$_1$–C$_6$-alkoxy or fluoro(C$_1$–C$_6$)-alkoxy;
R$^5$ and R$^6$ are independently from each other hydrogen or C$_1$–C$_6$-alkyl;
R$^7$ is hydrogen or C$_1$–C$_6$-alkyl;
R$^8$ is hydrogen or C$_1$–C$_6$-alkyl;
m is 1, 2 or 3; and
n is 0, 1 or 2;
or a pharmaceutically acceptable salt thereof.

2. The compound of formula I according to claim 1 wherein
R$^1$ is —(CH$_2$)$_n$—CO—NR$^5$R$^6$; —(CH$_2$)$_n$—COOR$^7$; —(CH$_2$)$_n$—CN; —(CH$_2$)$_n$—OR$^8$; or phenyl, which is unsubstituted or substituted by one to three substituents selected from halogen and fluoro(C$_1$–C$_6$)-alkyl;
R$^2$ is hydrogen or C$_1$–C$_6$-alkyl;
R$^3$ is hydrogen, C$_1$–C$_6$-alkyl, C$_3$–C$_6$-cycloalkyl or benzyl;
R$^4$ is halogen, fluoro(C$_1$–C$_6$)-alkyl, cyano, C$_1$–C$_6$-alkoxy or fluoro(C$_1$–C$_6$)-alkoxy;
R$^5$ and R$^6$ are independently from each other hydrogen or C$_1$–C$_6$-alkyl;
R$^7$ is hydrogen or C$_1$–C$_6$-alkyl;
R$^8$ is hydrogen or C$_1$–C$_6$-alkyl;
m is 1, 2 or 3; and
n is 0, 1 or 2;
or a pharmaceutically acceptable salt.

3. The compound of formula I according to claim 1 wherein
R$^1$ is —(CH$_2$)$_n$—CO—NR$^5$R$^6$; —(CH$_2$)$_n$—COOR$^7$; —(CH$_2$)$_n$—CN; —(CH$_2$)$_n$—OR$^8$; or phenyl, which is unsubstituted or substituted by one to three substituents selected from halogen and fluoro(C$_1$–C$_6$)-alkyl;
R$^2$ is halogen or C$_1$–C$_6$-alkyl;
R$^3$ is hydrogen, C$_1$–C$_6$-alkyl, C$_3$–C$_6$-cycloalkyl or benzyl;
R$^4$ is halogen, fluoro(C$_1$–C$_6$)-alkyl, cyano, C$_1$–C$_6$-alkoxy or fluoro(C$_1$–C$_6$)-alkoxy;
R$^5$ and R$^6$ are independently from each other hydrogen or C$_1$–C$_6$-alkyl;
R$^7$ is hydrogen or C$_1$–C$_6$-alkyl;
R$^8$ is hydrogen or C$_1$–C$_6$-alkyl;
m is 1, 2 or 3; and
n is 0, 1 or 2;
or a pharmaceutically acceptable salt thereof.

4. The compound of formula I according to claim 1 wherein
R$^1$ is —(CH$_2$)$_n$—CO—NR$^5$R$^6$; —(CH$_2$)$_n$—COOR$^7$; —(CH$_2$)$_n$—CN; —(CH$_2$)$_n$—OR$^8$; or phenyl, which is unsubstituted or substituted by one to three substituents selected from halogen and fluoro(C$_1$–C$_6$)-alkyl;
R$^2$ is hydrogen, halogen or C$_1$–C$_6$-alkyl;
R$^3$ is C$_3$–C$_6$-cycloalkyl or benzyl;
R$^4$ is halogen, fluoro(C$_1$–C$_6$)-alkyl, cyano, C$_1$–C$_6$-alkoxy or fluoro(C$_1$–C$_6$)-alkoxy;
R$^5$ and R$^6$ are independently from each other hydrogen or C$_1$–C$_6$-alkyl;
R$^7$ is hydrogen or C$_1$–C$_6$-alkyl;
R$^8$ is hydrogen or C$_1$–C$_6$-alkyl;
m is 1, 2 or 3; and
n is 0, 1 or 2;
or a pharmaceutically acceptable salt thereof.

5. The compound of formula I according to claim 1 wherein
R$^1$ is —(CH$_2$)$_n$—CO—NH$_2$; —(CH$_2$)$_n$—COOR$^7$; —(CH$_2$)$_n$—CN; —(CH$_2$)$_n$—OR$^8$; or phenyl, which is unsubstituted or substituted by one to three substituents selected from halogen and fluoro(C$_1$–C$_6$)-alkyl;
R$^2$ is hydrogen, halogen or C$_1$–C$_6$-alkyl;
R$^3$ is hydrogen, C$_1$–C$_6$-alkyl, C$_3$–C$_6$-cycloalkyl or benzyl;
R$^4$ is halogen, fluoro(C$_1$–C$_6$)-alkyl, cyano, C$_1$–C$_6$-alkoxy or fluoro(C$_1$–C$_6$)-alkoxy;
R$^5$ and R$^6$ are independently from each other hydrogen or C$_1$–C$_6$-alkyl;
R$^7$ is hydrogen or C$_1$–C$_6$-alkyl;
R$^8$ is hydrogen or C$_1$–C$_6$-alkyl;
m is 1, 2 or 3; and
n is 0, 1 or 2;
or a pharmaceutically acceptable salt thereof.

6. The compound of formula I according to claim 1 wherein

R$^1$ is —(CH$_2$)$_n$—CO—NR$^5$R$^6$; —(CH$_2$)$_n$—COOR$^7$; —(CH$_2$)$_n$—CN; —(CH$_2$)$_n$—OR$^8$; or phenyl, which is unsubstituted or substituted by one to three substituents selected from halogen and fluoro(C$_1$–C$_6$)-alkyl;

R$^2$ is hydrogen, halogen or C$_1$–C$_6$-alkyl;

R$^3$ is hydrogen, C$_1$–C$_6$-alkyl, C$_3$–C$_6$-cycloalkyl or benzyl;

R$^4$ is halogen, fluoro(C$_1$–C$_6$)-alkyl;

R$^5$ and R$^6$ are independently from each other hydrogen or C$_1$–C$_6$-alkyl;

R$^7$ is hydrogen or C$_1$–C$_6$-alkyl;

R$^8$ is hydrogen or C$_1$–C$_6$-alkyl;

m is 1, 2 or 3; and n is 0, 1 or 2;

or a pharmaceutically acceptable salt thereof.

7. The compound of formula I according to claim 1 wherein

R$^1$ is —(CH$_2$)$_n$—CO—NR$^5$R$^6$; —(CH$_2$)$_n$—COOR$^7$; —(CH$_2$)$_n$—CN; —(CH$_2$)$_n$—OR$^8$; or phenyl, which is unsubstituted or substituted by one to three substituents selected from halogen and fluoro(C$_1$–C$_6$)-alkyl;

R$^2$ is hydrogen, halogen or C$_1$–C$_6$-alkyl;

R$^3$ is hydrogen, C$_1$–C$_6$-alkyl, C$_3$–C$_6$-cycloalkyl or benzyl;

R$^4$ is C$_1$–C$_6$-alkoxy or fluoro(C$_1$–C$_6$)-alkoxy;

R$^5$ and R$^6$ are independently from each other hydrogen or C$_1$–C$_6$-alkyl;

R$^7$ is hydrogen or C$_1$–C$_6$-alkyl;

R$^8$ is hydrogen or C$_1$–C$_6$-alkyl;

m is 1, 2 or 3; and n is 0, 1 or 2;

or a pharmaceutically acceptable salt thereof.

8. The compound of formula I according to claim 1 wherein R$^1$ is —(CH$_2$)$_n$—CO—NR$^5$R$^6$.

9. The compound of formula I according to claim 1 wherein R$^1$ is —(CH$_2$)$_n$—COOR$^7$.

10. The compound of formula I according to claim 1 wherein R$^1$ is —(CH$_2$)$_n$—CN.

11. The compound of formula I according to claim 1 wherein R$^1$ is —(CH$_2$)$_n$—OR$^8$.

12. The compound of formula I according to claim 1 wherein R$^1$ is phenyl, which is unsubstituted or substituted by one to three substituents selected from halogen and fluoro(C$_1$–C$_6$)-alkyl.

13. The compound of formula I according to claim 12 wherein said phenyl is substituted by halogen.

14. The compound of formula I according to claim 1 wherein R$^2$ is hydrogen.

15. The compound of formula I according to claim 1 wherein R$^2$ is halogen.

16. The compound of formula I according to claim 1 wherein R$^2$ is C$_1$–C$_6$-alkyl.

17. The compound of formula I according to claim 1 wherein R$^3$ is benzyl.

18. The compound of formula I according to claim 1 wherein R$^4$ is halogen or fluoro(C$_1$–C$_6$)-alkyl.

19. The compound of formula I according to claim 1 wherein R$^4$ is cyano.

20. The compound of formula I according to claim 1 wherein R$^4$ is C$_1$–C$_6$alkoxy or fluoro(C$_1$–C$_6$)-alkoxy.

21. The compound of formula I according to claim 1 wherein R$^7$ is hydrogen.

22. The compound of formula I according to claim 1 wherein R$^7$ is (C$_1$–C$_6$)alkyl.

23. A compound of formula I according to claim 1 which is

2-[2-benzyl-7-(3-fluoro-benzyloxy)-4-oxo-4H-quinazolin-3-yl]-acetamide.

24. A process for the preparation of a compound of formula I according to claim 1 comprising reacting a compound of formula IV

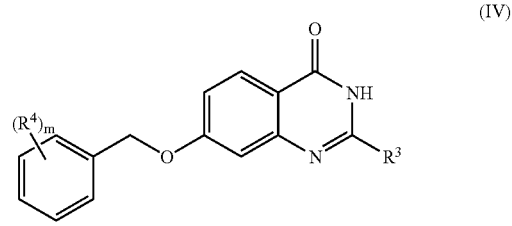

(IV)

wherein

R$^3$ is hydrogen, C$_1$–C$_6$-alkyl, C$_3$–C$_6$-cycloalkyl or benzyl;

R$^4$ is halogen, fluoro(C$_1$–C$_6$)-alkyl, cyano, C$_1$–C$_6$-alkoxy or fluoro(C$_1$–C$_6$)-alkoxy; and m is 1, 2 or 3 with a compound of formula V

(V)

wherein

R$^1$ is —(CH$_2$)$_n$—CO—NR$^5$R$^6$; —(CH$_2$)$_n$—COOR$^7$; —(CH$_2$)$_n$—CN; —(CH$_2$)$_n$—OR$^8$; or phenyl, which is unsubstituted or substituted by one to three substituents selected from halogen and fluoro(C$_1$–C$_6$)-alkyl;

R$^2$ is hydrogen, halogen or C$_1$–C$_6$-alkyl;

R$^5$ and R$^6$ are independently from each other hydrogen or C$_1$–C$_6$-alkyl;

R$^7$ is hydrogen or C$_1$–C$_6$-alkyl;

R$^8$ is hydrogen or C$_1$–C$_6$-alkyl; and n is 0, 1 or 2.

25. A pharmaceutical composition comprising a compound of formula I

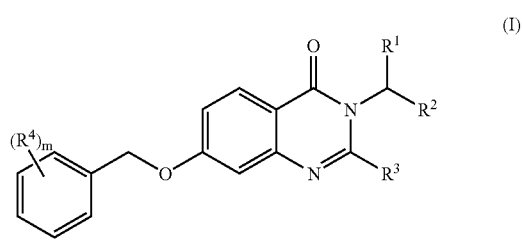

(I)

wherein

R$^1$ is —(CH$_2$)$_n$—CO—NR$^5$R$^6$; —(CH$_2$)$_n$—COOR$^7$; —(CH$_2$)$_n$—CN; —(CH$_2$)$_n$—OR$^8$; or phenyl, which is unsubstituted or substituted by one to three substituents selected from halogen and fluoro(C$_1$–C$_6$)-alkyl;

R$^2$ is hydrogen, halogen or C$_1$–C$_6$-alkyl;

R$^3$ is hydrogen, C$_1$–C$_6$-alkyl, C$_3$–C$_6$-cycloalkyl or benzyl;

R$^4$ is halogen, fluoro(C$_1$–C$_6$)-alkyl, cyano, C$_1$–C$_6$-alkoxy or fluoro(C$_1$–C$_6$)-alkoxy;

R[5] and R[6] are independently from each other hydrogen or $C_1-C_6$-alkyl;
R[7] is hydrogen or $C_1-C_6$-alkyl;
R[8] is hydrogen or $C_1-C_6$-alkyl;
m is 1, 2 or 3; and
n is 0, 1 or 2;
or a pharmaceutically acceptable salt thereof and a pharmaceutically acceptable carrier.

26. A compound of formula I

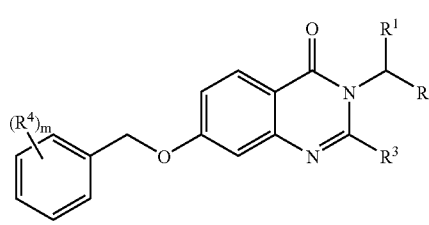

wherein
R[1] is —(CH$_2$)$_n$—CO—NR[5]R[6]; —(CH$_2$)$_n$—COOR[7]; —(CH$_2$)$_n$—NR[5]R[6]; —(CH$_2$)$_n$—CN; —(CH$_2$)$_n$—OR[8]; or phenyl, which is unsubstituted or substituted by one to three substituents selected from halogen and fluoro $(C_1-C_6)$-alkyl;
R[2] is hydrogen, halogen or $C_1-C_6$-alkyl;
R[3] is hydrogen, $C_1-C_6$-alkyl, or $C_3-C_6$-cycloalkyl;
R[4] is halogen, fluoro$(C_1-C_6)$-alkyl; cyano, $C_1-C_6$-alkoxy or fluoro$(C_1-C_6$-alkoxy;
R[5] and R[6] are independently from each other hydrogen or $C_1-C_6$-alkyl;
R[7] is hydrogen or $C_1-C_6$-alkyl;
R[8] is hydrogen or $C_1-C_6$-alkyl;
m is 1, 2 or 3; and
n is 0, 1 or 2;
or a pharmaceutically acceptable salt thereof.

27. The compound of formula I according to claim 26 wherein
R[1] is —(CH$_2$)$_n$—CO—NR[5]R[6]; —(CH$_2$)$_n$—COOR[7]; —(CH$_2$)$_n$—NR[5]R[6]; —(CH$_2$)$_n$—CN; —(CH$_2$)$_n$—OR[8]; or phenyl, which is unsubstituted or substituted by one to three substituents selected from halogen and fluoro $(C_1-C_6)$-alkyl;
R[2] is hydrogen, halogen or $C_1-C_6$-alkyl;
R[3] is hydrogen or $C_1-C_6$-alkyl,
R[4] is halogen, fluoro$(C_1-C_6)$-alkyl, cyano, $C_1-C_6$-alkoxy or fluoro$(C_1-C_6)$-alkoxy;
R[5] and R[6] are independently from each other hydrogen or $C_1-C_6$-alkyl;
R[7] is hydrogen or $C_1-C_6$-alkyl;
R[8] is hydrogen or $C_1-C_6$-alkyl;
m is 1, 2 or 3; and
n is 0, 1 or 2;
or a pharmaceutically acceptable salt thereof.

28. The compound of formula I according to claim 26 wherein R[1] is —(CH$_2$)$_n$—NR[5]R[6].

29. The compound of formula I according to claim 26 wherein R[3] is hydrogen.

30. The compound of formula I according to claim 26 wherein R[3] is $C_1-C_6$-alkyl.

31. The compound of formula I according to claim 26 wherein R[3] is $C_3-C_6$-cycloalkyl.

32. A compound of formula I according to claim 26 selected from
2-[7-(3-fluoro-benzyloxy)-4-oxo-4H-quinazolin-3-yl]-acetamide,
2-[7-(3-fluoro-benzyloxy)-4-oxo-4H-quinazolin-3-yl]-propionamide,
2-[7-(4-fluoro-benzyloxy)-4-oxo-4H-quinazolin-3-yl]-acetamide,
2-[7-(4-fluoro-benzyloxy)-4-oxo-4H-quinazolin-3-yl]-propionamide,
2-[7-(3-fluoro-benzyloxy)-2-methyl-4-oxo-4H-quinazolin-3-yl]-acetamide, and
2-[2-cyclopropyl-7-(3-fluoro-benzyloxy)-4-oxo-4H-quinazolin-3-yl]-acetamide.

33. A compound of formula I according to claim 26 selected from
7-(3-fluoro-benzyloxy)-3-(2-methoxy-ethyl)-3H-quinazolin-4-one,
7-(4-fluoro-benzyloxy)-3-(2-methoxy-ethyl)-3H-quinazolin-4-one,
7-(3-fluoro-benzyloxy)-3-(2-methoxy-ethyl)-2-methyl-3H-quinazolin-4-one,
3-(2-amino-ethyl)-7-(3-fluoro-benzyloxy)-3H-quinazolin-4-one 1:2 hydrochloride,
3-(3-amino-propyl)-7-(3-fluoro-benzyloxy)-3H-quinazolin-4-one 1:2 hydrochloride,
3-(2-amino-ethyl)-7-(4-fluoro-benzyloxy)-3H-quinazolin-4-one 1:1 hydrochloride, and
2-[7-(3-fluoro-benzyloxy)-2-methyl-4-oxo-4H-quinazolin-3-yl]-ethyl-ammonium chloride.

34. A compound of formula I according to claim 26 selected from
[7-(3-fluoro-benzyloxy)-4-oxo-4H-quinazolin-3-yl]-acetic acid ethyl ester;
fluoro-[7-(3-fluoro-benzyloxy)-4-oxo-4H-quinazolin-3-yl]-acetic acid ethyl ester;
2-[7-(3-fluoro-benzyloxy)-4-oxo-4H-quinazolin-3-yl]-propionic acid ethyl ester;
[7-(3-fluoro-benzyloxy)-4-oxo-4H-quinazolin-3-yl]-acetic acid tert-butyl ester;
2-[7-(3-fluoro-benzyloxy)-4-oxo-4H-quinazolin-3-yl]-propionic acid tert-butyl ester;
[7-(4-fluoro-benzyloxy)-4-oxo-4H-quinazolin-3-yl]-acetic acid ethyl ester; and
2-[7-(4-fluoro-benzyloxy)-4-oxo-4H-quinazolin-3-yl]-propionic acid ethyl ester.

35. The compound of formula I according to claim 26 wherein
R[1] is —(CH$_2$)$_n$—CO—NR[5]R[6]; —(CH$_2$)$_n$—COOR[7]; —(CH$_2$)$_n$—NR[5]R[6]; —(CH$_2$)$_n$—CN; —(CH$_2$)$_n$—OR[8]; or phenyl, which is unsubstituted or substituted by one to three substituents selected from halogen and fluoro $(C_1-C_6)$-alkyl;
R[2] is hydrogen or $C_1-C_6$-alkyl;
R[3] is hydrogen, $C_1-C_6$-alkyl, or $C_3-C_6$-cycloalkyl;
R[4] is halogen, fluoro$(C_1-C_6)$-alkyl; cyano, $C_1-C_6$-alkoxy or fluoro$(C_1-C_6$-alkoxy;
R[5] and R[6] are independently from each other hydrogen or $C_1-C_6$-alkyl;
R[7] is hydrogen or $C_1-C_6$-alkyl;
R[8] is hydrogen or $C_1-C_6$-alkyl;
m is 1, 2 or 3; and
n is 0, 1 or 2;
or a pharmaceutically acceptable salt.

36. The compound of formula I according to claim 26 wherein R[1] is —(CH$_2$)$_n$—CO—NR[5]R[6]; —(CH$_2$)$_n$—COOR[7]; —(CH$_2$)$_n$—NR[5]R[6]; —(CH$_2$)$_n$—CN; —(CH$_2$)$_n$—

OR$^8$; or phenyl, which is unsubstituted or substituted by one to three substituents selected from halogen and fluoro (C$_1$–C$_6$)-alkyl;
R$^2$ is halogen or C$_1$–C$_6$-alkyl;
R$^3$ is hydrogen, C$_1$–C$_6$-alkyl, or C$_3$–C$_6$-cycloalkyl;
R$^4$ is halogen, fluoro(C$_1$–C$_6$)-alkyl; cyano, C$_1$–C$_6$-alkoxy or fluoro(C$_1$–C$_6$-alkoxy);
R$^5$ and R$^6$ are independently from each other hydrogen or C$_1$–C$_6$-alkyl;
R$^7$ is hydrogen or C$_1$–C$_6$-alkyl;
R$^8$ is hydrogen or C$_1$–C$_6$-alkyl;
m is 1, 2 or 3; and
n is 0, 1 or 2;
or a pharmaceutically acceptable salt thereof.

37. The compound of formula I according to claim 26 wherein
R$^1$ is —(CH$_2$)$_n$—CO—NR$^5$R$^6$; —(CH$_2$)$_n$—COOR$^7$; —(CH$_2$)$_n$—NR$^5$R$^6$; —(CH$_2$)$_n$—CN; —(CH$_2$)$_n$—OR$^8$; or phenyl, which is unsubstituted or substituted by one to three substituents selected from halogen and fluoro (C$_1$–C$_6$)-alkyl;
R$^2$ is hydrogen, halogen or C$_1$–C$_6$-alkyl;
R$^3$ is C$_3$–C$_6$-cycloalkyl;
R$^4$ is halogen, fluoro(C$_1$–C$_6$)-alkyl; cyano, C$_1$–C$_6$-alkoxy or fluoro(C$_1$–C$_6$-alkoxy);
R$^5$ and R$^6$ are independently from each other hydrogen or C$_1$–C$_6$-alkyl;
R$^7$ is hydrogen or C$_1$–C$_6$-alkyl;
R$^8$ is hydrogen or C$_1$–C$_6$-alkyl;
m is 1, 2 or 3; and
n is 0, 1 or 2;
or a pharmaceutically acceptable salt thereof.

38. The compound of formula I according to claim 26 wherein
R$^1$ is —(CH$_2$)$_n$—CO—NH$_2$; —(CH$_2$)$_n$—COOR$^7$; —(CH$_2$)$_n$—NH$_2$; —(CH$_2$)$_n$—CN; —(CH$_2$)$_n$—OR$^8$; or phenyl, which is unsubstituted or substituted by one to three substituents selected from halogen and fluoro (C$_1$–C$_6$)-alkyl;
R$^2$ is hydrogen, halogen or C$_1$–C$_6$-alkyl;
R$^3$ is hydrogen, C$_1$–C$_6$-alkyl, or C$_3$–C$_6$-cycloalkyl;
R$^4$ is halogen, fluoro(C$_1$–C$_6$)-alkyl; cyano, C$_1$–C$_6$-alkoxy or fluoro(C$_1$–C$_6$-alkoxy);
R$^5$ and R$^6$ are independently from each other hydrogen or C$_1$–C$_6$-alkyl;
R$^7$ is hydrogen or C$_1$–C$_6$-alkyl;
R$^8$ is hydrogen or C$_1$–C$_6$-alkyl;
m is 1, 2 or 3; and
n is 0, 1 or 2;
or a pharmaceutically acceptable salt thereof.

39. The compound of formula I according to claim 26 wherein
R$^1$ is —(CH$_2$)$_n$—CO—NR$^5$R$^6$; —(CH$_2$)$_n$—COOR$^7$; —(CH$_2$)$_n$—NR$^5$R$^6$; —(CH$_2$)$_n$—CN; —(CH$_2$)$_n$—OR$^8$; or phenyl, which is unsubstituted or substituted by one to three substituents selected from halogen and fluoro (C$_1$–C$_6$)-alkyl;
R$^2$ is hydrogen, halogen or C$_1$–C$_6$-alkyl;
R$^3$ is hydrogen, C$_1$–C$_6$-alkyl, or C$_3$–C$_6$-cycloalkyl;
R$^4$ is halogen, fluoro(C$_1$–C$_6$)-alkyl;
R$^5$ and R$^6$ are independently from each other hydrogen or C$_1$–C$_6$-alkyl;
R$^7$ is hydrogen or C$_1$–C$_6$-alkyl;
R$^8$ is hydrogen or C$_1$–C$_6$-alkyl;
m is 1, 2 or 3; and
n is 0, 1 or 2;
or a pharmaceutically acceptable salt thereof.

40. The compound of formula I according to claim 26 wherein
R$^1$ is —(CH$_2$)$_n$—CO—NR$^5$R$^6$; —(CH$_2$)$_n$—COOR$^7$; —(CH$_2$)$_n$—NR$^5$R$^6$; —(CH$_2$)$_n$—CN; —(CH$_2$)$_n$—OR$^8$; or phenyl, which is unsubstituted or substituted by one to three substituents selected from halogen and fluoro (C$_1$–C$_6$)-alkyl;
R$^2$ is hydrogen, halogen or C$_1$–C$_6$-alkyl;
R$^3$ is hydrogen, C$_1$–C$_6$-alkyl, or C$_3$–C$_6$-cycloalkyl;
R$^4$ is C$_1$–C$_6$-alkoxy or fluoro(C$_1$–C$_6$-alkoxy);
R$^5$ and R$^6$ are independently from each other hydrogen or C$_1$–C$_6$-alkyl;
R$^7$ is hydrogen or C$_1$–C$_6$-alkyl;
R$^8$ is hydrogen or C$_1$–C$_6$-alkyl;
m is 1, 2 or 3; and
n is 0, 1 or 2;
or a pharmaceutically acceptable salt thereof.

41. The compound of formula I according to claim 26 wherein R$^2$ is hydrogen.

42. The compound of formula I according to claim 26 wherein R$^2$ is halogen.

43. The compound of formula I according to claim 26 wherein R$^2$ is C$_1$–C$_6$-alkyl.

44. The compound of formula I according to claim 26 wherein R$^4$ is halogen or fluoro(C$_1$–C$_6$)-alkyl.

45. The compound of formula I according to claim 26 wherein R$^4$ is cyano.

46. The compound of formula I according to claim 26 wherein R$^4$ is C$_1$–C$_6$-alkoxy or fluoro(C$_1$–C$_6$-alkoxy).

47. The compound of formula I according to claim 26 wherein R$^7$ is hydrogen.

48. The compound of formula I according to claim 26 wherein R$^7$ is (C$_1$–C$_6$)-alkyl.

49. A compound of formula I according to claim 26 selected from
3-(3-fluoro-benzyl)-7-(3-fluoro-benzyloxy)-3H-quinazolin-4-one;
3-[7-(4-fluoro-benzyloxy)-4-oxo-4H-quinazolin-3-yl]-propionamide;
2-[7-(3-fluoro-benzyloxy)-2-isopropyl-4-oxo-4H-quinazolin-3-yl]-acetamide;
[7-(3-fluoro-benzyloxy)-2-isopropyl-4-oxo-4H-quinazolin-3-yl]-acetonitrile;
2-cyclopropyl-7-(3-fluoro-benzyloxy)-3-(2-methoxy-ethyl)-3H-quinazolin-4-one; and
[2-cyclopropyl-7-(3-fluoro-benzyloxy)-4-oxo-4H-quinazolin-3-yl]-acetic acid methyl ester.

50. A pharmaceutical composition comprising a compound of formula I

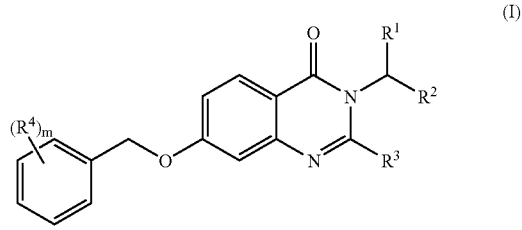

wherein
R$^1$ is —(CH$_2$)$_n$—CO—NR$^5$R$^6$; —(CH$_2$)$_n$—COOR$^7$; —(CH$_2$)$_n$—NR$^5$R$^6$; —(CH$_2$)$_n$—CN; —(CH$_2$)$_n$—OR$^8$;

or phenyl, which is unsubstituted or substituted by one to three substituents selected from halogen and fluoro $(C_1-C_6)$-alkyl;

$R^2$ is hydrogen, halogen or $C_1-C_6$-alkyl;

$R^3$ is hydrogen, $C_1-C_6$-alkyl, or $C_3-C_6$-cycloalkyl;

$R^4$ is halogen, fluoro$(C_1-C_6)$-alkyl, cyano, $C_1-C_6$-alkoxy or fluoro$(C_1-C_6)$-alkoxy;

$R^5$ and $R^6$ are independently from each other hydrogen or $C_1-C_6$-alkyl;

$R^7$ is hydrogen or $C_1-C_6$-alkyl;

$R^8$ is hydrogen or $C_1-C_6$-alkyl;

m is 1, 2 or 3; and n is 0, 1 or 2;

or a pharmaceutically acceptable salt thereof and a pharmaceutically acceptable carrier.

* * * * *